United States Patent
Kurono et al.

(10) Patent No.: US 8,206,324 B2
(45) Date of Patent: Jun. 26, 2012

(54) METHOD FOR MONITORING LIVING BODY ACTIVITIES, AND OPTICAL FIBER TYPE FLAT SHAPED BODY SENSOR, GARMENT STYLED OPTICAL FIBER TYPE FLAT SHAPED BODY SENSOR AND HUMAN BODY FITTED OPTICAL FIBER TYPE FLAT SHAPED BODY SENSOR USED FOR THE SAME

(75) Inventors: Masahiro Kurono, Komae (JP); Shiro Matsuo, Osaka (JP); Akira Yuto, Osaka (JP); Shinya Meguri, Osaka (JP); Toshitaka Maeno, Osaka (JP); Hiroshige Matsuda, Osaka (JP); Kenichi Suzuki, Osaka (JP); Kazuhiko Taniguchi, Osaka (JP); Kokichi Kato, Osaka (JP)

(73) Assignee: Kinden Corporation, Osaka (JP)

( * ) Notice: Subject to any disclaimer, the term of this patent is extended or adjusted under 35 U.S.C. 154(b) by 901 days.

(21) Appl. No.: 12/038,742

(22) Filed: Feb. 27, 2008

(65) Prior Publication Data
US 2008/0221488 A1 Sep. 11, 2008

Related U.S. Application Data

(63) Continuation-in-part of application No. PCT/JP2006/317297, filed on Aug. 25, 2006.

(30) Foreign Application Priority Data

Aug. 30, 2005 (JP) ................................ 2005-250154

(51) Int. Cl.
*A61B 5/103* (2006.01)
*A61B 5/117* (2006.01)
(52) U.S. Cl. .......... 600/595; 600/301; 600/587; 356/32; 385/12; 385/13

(58) Field of Classification Search .......... 600/300–301, 600/481, 483–484, 502, 529, 587, 595; 356/32–35.5, 356/491–494, 901, 911; 385/1–13
See application file for complete search history.

(56) References Cited

U.S. PATENT DOCUMENTS
3,700,334 A * 10/1972 Low et al. ................... 356/453
(Continued)

FOREIGN PATENT DOCUMENTS
WO 2004/112611 A1 12/2004
(Continued)

OTHER PUBLICATIONS

Article titled "Survey of Methods for the Complete Determination of a State of Polarization," by P.S. Hauge in SPIE, vol. 88, Polarized Light, pp. 3-10, 1976.*

(Continued)

*Primary Examiner* — Rene Towa
(74) *Attorney, Agent, or Firm* — Griffin & Szipl, P.C.

(57) ABSTRACT

A living body monitoring activity system detects major activities, or feeble living body activities. In a method for monitoring existence of human movements or living body activities in living environments (e.g., sleeping activities involving a bed, a Futon-mat, a pad, or a Tatami-mat), an optical fiber type flat shaped body sensor including an optical fiber affixed or fitted to a flat shaped body is used, and light is emitted into the optical fiber from a light source, and changes of polarized wave conditions of light propagating in the optical fiber are brought about by changes in form of the optical fiber type flat shaped body sensor caused by human movements or living body activities and are detected by a measuring apparatus for polarized wave fluctuations so human activities or movements are discriminated based on the detected value of the polarized wave fluctuations.

12 Claims, 15 Drawing Sheets

U.S. PATENT DOCUMENTS

| | | | |
|---|---|---|---|
| 4,692,610 A * | 9/1987 | Szuchy | 250/227.14 |
| 5,134,386 A * | 7/1992 | Swanic | 340/541 |
| 5,212,379 A * | 5/1993 | Nafarrate et al. | 250/227.14 |
| 5,754,293 A * | 5/1998 | Farhadiroushan | 356/478 |
| 5,846,206 A * | 12/1998 | Bader | 600/534 |
| 6,141,466 A * | 10/2000 | Shigehara | 385/22 |
| 6,498,652 B1 * | 12/2002 | Varshneya et al. | 356/477 |
| 6,816,260 B2 | 11/2004 | Peupelmann et al. | |
| 2002/0044282 A1 * | 4/2002 | Moeller et al. | 356/369 |
| 2003/0002041 A1 | 1/2003 | Peupelmann et al. | |
| 2004/0082874 A1 * | 4/2004 | Aoki et al. | 600/534 |
| 2004/0136636 A1 * | 7/2004 | Rogers | 385/11 |
| 2004/0210155 A1 * | 10/2004 | Takemura et al. | 600/534 |
| 2006/0072922 A1 * | 4/2006 | MacDonald et al. | 398/152 |
| 2006/0152378 A1 * | 7/2006 | Lokhorst et al. | 340/666 |
| 2006/0262307 A1 * | 11/2006 | Peupelmann et al. | 356/364 |
| 2006/0278240 A1 * | 12/2006 | Spillman et al. | 128/898 |
| 2007/0008156 A1 * | 1/2007 | Ueda et al. | 340/575 |
| 2008/0068606 A1 * | 3/2008 | Rogers et al. | 356/365 |

FOREIGN PATENT DOCUMENTS

| | | |
|---|---|---|
| WO | 2005/116601 A2 | 12/2005 |

OTHER PUBLICATIONS

Gary Cloud, Optical Methods—Back to Basics, Experimental Techniques 27-29 (2007).

Polarization, at http://electron9.phys.utk.edu/optica421/modules/m8/polarization.htm, downloaded on Jul. 26, 2011, eleven pages, filed herewith as Exhibit A.

P. Ewart, Optics, an e-book downloaded on Jul. 27, 2011 from http://www.scribd.com/doc/49640060/57/Interference-of-polarized-light, filed herewith as Exhibit B.

* cited by examiner (a)

(b)

(c)

(a)

(b)

(c)

(a)

(b)

(c)

(d)

METHOD FOR MONITORING LIVING BODY ACTIVITIES, AND OPTICAL FIBER TYPE FLAT SHAPED BODY SENSOR, GARMENT STYLED OPTICAL FIBER TYPE FLAT SHAPED BODY SENSOR AND HUMAN BODY FITTED OPTICAL FIBER TYPE FLAT SHAPED BODY SENSOR USED FOR THE SAME

This is a Continuation or Continuation-in-Part of International Patent Application No. PCT/JP2006/317297 filed Aug. 25, 2006, which claims priority on Japanese Patent Application No. 2005-250154, filed Aug. 30, 2005. The entire disclosures of the above patent applications are hereby incorporated by reference.

TECHNICAL FIELD

The present invention is mainly utilized in fields such as medical care or nursing care and the like, and relates to a method for monitoring living body activities or movements on a floor, a bed or a Tatami-mat, and the like, which makes it possible for human body activities or movements to be sensed or monitored from a distance both automatically and with high accuracy, and the invention includes an optical fiber type flat shaped body sensor used for the same. More specifically, the present invention relates to a method for monitoring living body activities, which makes it possible for all human body activities and movements including respiration, pulsation and the like, to be detected with high accuracy under exactly the same conditions as those of ordinary living environments without using a purpose-made bed, a special-made Futon-bed, and the like. The method for monitoring living body activities, in accordance with the invention, employs means of detecting fluctuations of a polarized wave of light inside an optical fiber brought about by human activities on a bed sheet, a mat, a pad, a Tatami-mat, a floor cover, a carpet, and the like, and monitoring of living body activities underneath a quilt cover or a blanket by utilizing an optical fiber incorporated bed sheet, quilt, blanket, mat, pad, Tatami-mat, floor cover, carpet and the like (hereafter called an "optical fiber type flat shaped body sensor"), wherein monitoring is achieved with the aid of a highly sensitive polarized wave fluctuations measuring apparatus, and an optical fiber type flat shaped body sensor, a garment styled optical fiber type flat shaped body sensor, and a human body fitted optical fiber type flat shaped body sensor used for the same.

TECHNICAL BACKGROUND

Conventionally, in the field of medical care, nursing care and the like, a distance monitoring system (i.e., remote monitoring system) for so-called nursing care, and the like, has been developed aiming at providing effective nursing with less staff by means of detecting movements of a patient, those cared for, and the like, in a hospital room wherein movement detection is conveyed to a nurse station or a ward through a cable or cable-free system. At the present time, the further development of this kind of a remote monitoring system is actively under way.

In recent years, monitoring systems employing an optical fiber as a monitoring sensor for monitoring living body activities have received widespread attention because of the excellent detection sensitivity and stability of the optical fiber. Specifically, while a conventional piezoelectric sensor or a vibration type sensor may be used to accurately detect, to some extent, human movements such as going to bed, rising from bed, or tossing and turning in bed, and the like, it is difficult to detect certain human movements, including respiration and pulse, with high accuracy by using a piezoelectric sensor or a vibration type sensor.

A monitoring system for detecting living body activities that employs an optical fiber is disclosed, for example, by Japanese Unexamined Patent Application No. 5-312966, by Japanese Unexamined Patent Application No. 8-584, and the like.

The aforementioned sensor technologies are all based on the fact that "when an optical fiber is abruptly bent, a linearity of light surpasses a light enclosure effect of light of the optical fiber core, thus bringing about the loss of a quantity of light due to the leakage of light". However, there remain several disadvantages of these sensor technologies such as listed below in items a, b and c:

a. The optical fiber needs to be bent abruptly in order that a loss is brought about;

b. It is difficult to adjust the bending quantity due to the fact that loss increases exponentially to the bend radius. Thus, a specially designed tool is required to obtain an appropriate bend quantity;

c. There is a concern that the wire (optical fiber) may be broken or deteriorate due to fatigue when it is abruptly bent.

On the other hand, with optical fibers, it has been well known for a long time that the polarized wave conditions of the propagated light changes with changes of the shape of the optical fiber due to bending. Detecting systems for crime prevention have been developed based on this fact. For example, Japanese Unexamined Patent Application Publication No. 2000-40187, Japanese Unexamined Patent Application Publication No. 2001-6055 and the like, disclose an optical fiber fitted to a fence, and the like, in order to sense invaders and raise an alarm by means of detecting polarized wave fluctuations brought about by external forces applied to the optical fiber.

However, with Japanese Unexamined Patent Application Publication No. 2000-40187, and the like, the device disclosed is constituted so that the optical fiber is simply fitted to the fence for the purpose of sensing invaders approaching from outside. Therefore, it is difficult to immediately apply this technology for purposes of monitoring living body activities of a human being. In addition, because the device disclosed by Japanese Unexamined Patent Application Publication No. 2000-40187, and the like, is constituted so that external forces generated by an invader is directly applied to the optical fiber, and no consideration at all is made to enhance the sensitivity of detecting fluctuations of polarized wave conditions due to changes occurring when feeble pressure is applied, it would be difficult for a person of ordinary skill to immediately apply this sensing technology to a monitoring system for monitoring other human activities such as respiration and heart pulsation.

In addition, because polarized wave conditions of light traveling in an optical fiber are generally random, a so-called "polarized wave correction" is required in order to use the polarized wave as a sensor. However, the polarized wave correction is time-consuming to achieve, and then manufacturing costs go up because the apparatus for measuring polarized wave fluctuations is so complicated.

Applicants of the present invention have developed and disclosed a system with which a polarized wave quantity is detected in a simple manner and with high sensitivity in order to solve problems pertaining to detecting fluctuations of a polarized wave without requiring corrections of the polarized wave (Japanese Unexamined Patent Application Publication No. 2004-108918 and Japanese Unexamined Patent Application Publication No. 2004-184223). The present invention makes it possible to detect (or sense) all human activities and movements, including respiration and heart pulsation, with high accuracy by means of applying the system for detecting the quantity of polarized wave fluctuations to a system for monitoring activities and movements of a human.

[Patent Document 1] Japanese Unexamined Patent Application Publication No. 5-312966.
[Patent Document 2] Japanese Unexamined Patent Application Publication No. 8-584.
[Patent Document 3] Japanese Unexamined Patent Application Publication No. 2000-40187.
[Patent Document 4] Japanese Unexamined Patent Application Publication No. 2001-6055.
[Patent Document 5] Japanese Unexamined Patent Application Publication No. 2004-108918.
[Patent Document 6] Japanese Unexamined Patent Application Publication No. 2004-184223.

Objects of the Invention

It is a principal object of the present invention to provide a method for monitoring living body activities, and an optical fiber type flat shaped body sensor, a garment styled optical fiber type flat shaped body sensor, and a human body fitted optical fiber type flat shaped body sensor to be used for the method, in order to solve the aforementioned problems with known monitoring systems for living body activities such as:

a. the fact that it is not possible to monitor respiration, pulse, and the like, of a human at low costs and with high accuracy by using a conventional system employing a piezoelectric sensor or a vibration type sensor;

b. with a conventional system employing an optical fiber as a sensor, it is difficult to detect changes of feeble or low movement living body activities (such as, for example, respiration and pulse) because the detection element relies upon loss of a light quantity brought about by abrupt bending of an optical fiber, and with the conventional system there exists a risk that bending of wire (optical fiber) may cause it to break or deteriorate; and c. there is a problem with low detection sensitivity because the conventional monitoring system that utilizes fluctuations of the polarized wave as the detection element are mainly used for preventing intruder invasion from outside. It is, therefore, an object of the present invention to make it possible that a sensor for monitoring human activity is provided that can be used in the same way as a conventional cloth sheet is used, and wherein a quantity of polarized wave fluctuations of propagated light in an optical fiber is brought about by human activities, such as respiration, heart pulsation, and the like, which can be detected with high sensitivity by sensing human activities with high accuracy. It is another object of the present invention to make it possible that sensors can be manufactured at low costs.

More specifically, it is a principal object of the present invention to provide:

a. an optical fiber type flat shaped body sensor that allows patient monitoring, and the like, without adversely affecting the monitored patient while sleeping by integrating a flat shaped body, such as a cloth made sheet, with the aforementioned optical fiber so as to make use of features of the light and thin thread-like optical fiber so that the optical fiber may be used as a conventional cloth made sheet is used (i.e., as a blanket or sheet);

b. an optical fiber type flat shaped body sensor that is adaptable to a variety of human activities under many possible circumstantial settings and forms (for example, a bed, a Tatami-mat, a bed sheet, a seat cover, a stretcher, a hammock, a carpet, a mat, clothes, and the like); and c. a method for monitoring living body activities that makes it possible to detect with high accuracy various kinds of vibrations, having a wide variety of vibration characteristics, by using a polarized wave fluctuation measuring apparatus and by treating signals thereof in a special way even though there exist human activities or movements that bring about predictable changes in the flat shaped body-like sheet, and the like, and to detect human activities or movements, such as respiration or pulse, which conversely bring about little change in the form of a flat shaped body, and to detect vibrations that are feeble when the feeble vibrations make direct contact with the fiber, or when changes of the flat shaped body lead to changes of the fiber, or when changes of the flat shaped body and the fiber are brought about by way of a pad.

DISCLOSURE OF THE INVENTION

To overcome difficulty with the aforementioned devices, the present invention, in accordance with a first embodiment, is fundamentally constituted to include a method for monitoring the existence of movements of human or living body activities under living circumstances such as while sleeping on a bed, Futon-bed, pad, Tatami-mat and the like, wherein human activities or movements are discriminated using the detected value of polarized wave fluctuations. In particular, the method, in accordance with a first embodiment of the invention, includes the steps of: (a) disposing an optical fiber type flat shaped body sensor comprising a flat shaped body and an optical fiber fitted to or integrated with the flat shaped body so that living body activities or movements of a human being bring about changes in form of the optical fiber type flat shaped body sensor; (b) emitting light into the optical fiber from a light source; (c) producing fluctuations in a polarized wave of light propagated in the optical fiber when living body activities or movements of the human being bring about changes in form of the optical fiber type flat shaped body sensor; (d) detecting fluctuations in the polarized wave of light using a polarized wave fluctuations measuring apparatus (a.k.a. measuring apparatus for polarized wave fluctuations); and (e) discriminating human activities or movements using the detected fluctuations in the polarized wave of light.

The present invention, in accordance with a second embodiment of the invention, further modifies the first embodiment so that the flat shaped body is to be any of a sheet, a bed sheet, a blanket, a mat, a pad, a Tatami-mat, a floor cover or a carpet. The present invention, in accordance with a third embodiment, further modifies the first embodiment so that periodic vibrations specific to respiration or heart pulsation are detected using the sum of the power spectrum detected by the polarized wave fluctuations measuring apparatus for polarized wave fluctuations of light propagated in the optical fiber, and by time wave forms of 3 stokes parameters that represent polarized wave conditions of light being transformed with a Fourier Transform, respectively.

The present invention, in accordance with a fourth embodiment of the present invention, further modifies the first or third embodiments so that it becomes possible that using the measuring apparatus for polarized wave fluctuations of light propagating in an optical fiber, detection of living body activities or movements of the human subject are detected at high velocity and with high sensitivity so that the difference between the present value of a polarized wave condition parameter expressed by 3 stokes parameters, a polarized wave ellipse or a phase difference between orthogonally polarized waves (wherein "orthogonally polarized waves" refer to polarized waves in which their directions of forward movement intersect at a right angle), and the like, and a polarized wave condition parameter found ¼ to ½ hours before the specific periodicity of vibration obtained with the aforementioned third embodiment is computed as a polarized wave fluctuation quantity. The present invention, in accordance with a fifth embodiment of the present invention, further modifies the third or fourth embodiments so that it becomes possible that highly sensitive living body activities or movements of the human are detected so that, at a time of computing the polarized wave fluctuation quantity, the polarized wave condition parameter obtained from sampling is processed for a moving average, and the width of the moving average is made to be ¼ to ½ the vibration periodicity obtained in the third embodiment and the like, thus effectively removing random noise from signals employed for discriminating human activities or movements. The present invention, in accordance with a sixth embodiment of the invention, further modifies the first and third to fifth embodiments so that not only the existence of human activities but also the type of human activities are discriminated by utilizing the fact that for body movements, such as tossing and turning, the polarized wave fluctuation signal is aperiodic and the fluctuation range is wide, while for the events of respiration at rest or heart pulsation during periods of no respiring, the fluctuation range is narrow and periodic. The present invention, in accordance with a seventh embodiment, further modifies the third embodiment so that it becomes possible that when the human being intentionally kicks or knocks any given side of the flat shaped body, then signals are transmitted by the measuring apparatus for polarized wave fluctuations with characteristic patterns.

The present invention, in accordance with an eighth embodiment of the invention, further modifies the first embodiment so that a plurality of optical fiber type flat shaped body sensors or a plurality of optical fibers in blocks disposed in the optical fiber type flat shaped body sensor are monitored in sequence using one set of the measuring apparatus for polarized wave fluctuations by means that a light source apparatus and the polarized wave fluctuations measuring apparatus are switched and connected to the plurality of optical fibers of optical fiber type flat shaped body sensors or to the plurality of optical fibers in blocks disposed in the optical fiber type flat shaped body sensor. The present invention, in accordance with a ninth embodiment of the invention, further modifies the first embodiment found so that a plurality of optical fibers of the flat shaped body sensor or a plurality of blocks in the optical fiber type flat shaped body sensor are monitored in sequence using one set of a measuring apparatus for polarized wave fluctuations by means that light is emitted to the plurality of optical fibers of the optical fiber type flat shaped body sensors or the plurality of optical fibers in blocks in the optical fiber type flat shaped body sensor from a wavelength variable light source by switching optical fibers in sequence using a wavelength separation filter.

The present invention, in accordance with a tenth embodiment of the present invention, further modifies the first embodiment so that a specific block of the optical fiber is discriminated for monitoring by means of a plurality of filters, with which a specific wave length such as an optical fiber diffraction is reflected, wherein the plurality of filters are incorporated at some midpoint of the optical fiber of the optical fiber type flat shaped body sensor, thus the wave length of the light source is changed. The present invention, in accordance with an eleventh embodiment of the invention, further modifies the first embodiment so that a specific block of the optical fiber is discriminated for monitoring using a delay time of light dispersed in the optical fiber by transmitting an optical pulse from one end of the optical fiber of the optical fiber type flat shaped body sensor. The present invention, in accordance with a twelfth embodiment of the present invention, further modifies a first embodiment so that movements of the human are monitored from a distance by making the optical fiber type flat shaped body sensor include a communications optical fiber and by connecting the optical fiber to the communications optical fiber.

The present invention, in accordance with a thirteenth embodiment, is fundamentally constituted so that an optical fiber type flat shaped body sensor is provided that includes: (a) a flat shaped body; and (b) one or more optical fibers affixed to and running throughout the flat shaped body so that shape changes of any part of an outer surface of the flat shaped body are reflected as a shape change in form of one or more of the optical fibers.

The present invention, in accordance with a fourteen embodiment, further modifies the thirteenth embodiment so that similar use-feelings as those obtained with cloth made sheets, such as when the sensor is employed while the human being is in bed, are achieved and so that the sensor employs extremely thin optical fibers that are sewed up throughout the flat shaped body, thus weight (i.e., cloth weight), thickness and flexibility of the optical fiber incorporated in the flat shaped body remain unchanged compared with those of an ordinary cloth made sheet. The present invention, in accordance with a fifteenth embodiment of the invention, further modifies the thirteenth and fourteenth embodiments so that the flat shaped body is made to be any one of a sheet, a bed sheet, a quilt cover, a blanket, a mat, a pad, a Tatami-mat, a floor cover or a carpet. The present invention, in accordance with a sixteenth embodiment of the present invention, further modifies the thirteenth or fourteenth embodiments so that sensor sensitivity brought about by using polarized wave fluctuations is raised or increased with respect to changes in form of the optical fiber type flat shaped body sensor by affixing or sewing up of the optical fiber with the flat shape body so as to cause the optical fiber to form a complex like linear shaped, wave shaped or loop shaped form. The present invention, in accordance with a seventeenth embodiment, further modifies the thirteenth or fourteenth embodiments so that sensor sensitivity brought about by the polarized wave fluctuations is raised or increased with respect to changes in form of the optical fiber type flat shaped body sensor by multiplying the number of conductors used to make the optical fiber. The present invention, in accordance with an eighteenth embodiment of the present invention, further modifies the thirteenth or fourteenth embodiments so that sensor sensitivity brought about by using polarized wave fluctuations is raised or increased with respect to changes in form of the optical fiber type flat shaped body sensor by placing a reflection mirror on one side of the optical fiber so that light signals are transmitted in the optical fiber with to-and-from movements. The present invention, in accordance with a nineteenth embodiment of the present invention, further modifies the thirteenth or fourteenth embodiments so that the optical fiber type flat shaped body sensor is processed to make a cover for a Futon-bed, a quilt, a mat, a sofa, and the like. The present invention, in accordance with a twentieth embodiment of the present invention, further modifies the nineteenth embodiment so that a water tight process is conducted to provide the sensor with a vinyl cover and the like.

The present invention, in accordance with a twenty-first embodiment, pertains to a garment styled optical fiber type flat shaped body sensor that includes (a) a flat shaped body, wherein the flat shaped body is a garment to be worn by a human being to be monitored; and (b) one or more optical fibers affixed to and running throughout the flat shaped body so that shape changes of any part of the flat shaped body are reflected as a shape change in form of one or more of the optical fibers, wherein changes in form of a part of the human body of the human being monitored are reflected as changes in form of one or more of the optical fibers, wherein the one or more optical fibers are sewed up in, or affixed to, the garment that is disposed on the body of the human being while in bed so that the human being is monitored for activity conditions and the like during a medical test being conducted, wherein the garment is selected from the group consisting of pajamas, night wear, a patient dress, or other garment to be worn when the human undergoes monitoring.

The present invention, in accordance with a twenty-second embodiment, pertains to a human body fitted optical fiber type flat shaped body sensor that includes (a) a flat shaped body, wherein the flat shaped body is a human body fitted pad in the shape of a stomach band, a bandage, or a sheet; and (b) an optical fiber affixed to and running throughout the flat shaped body so that shape changes of any part of the flat shaped body are reflected as a shape change in form of the optical fiber, wherein changes in form of any part of the human body fitted to the human body fitted pad are reflected as changes in form of the optical fiber, wherein the optical fiber is sewed up in, or affixed to, the human body fitted pad.

Effect of the Invention

The present invention makes it possible that movements of a patient, and the like, may be monitored under normal conditions encountered in daily life without giving the users (e.g., patients) of the optical fiber type flat shaped body sensor any strange or abnormal feelings because the optical fiber type flat shaped body sensor is formed of light weight optical fibers having a small diameter that are integrated with, and affixed to, a flat shaped body such as a cloth made sheet, and the like.

The present invention makes it possible that a wide range of vibration intensity generated from human activities, like getting into bed and getting out of bed to feeble vibration generating activities such as respiration and heart pulsation, may be detected with high accuracy by using one measuring apparatus for polarized wave fluctuations. The present invention is generally applicable to all flat shaped bodies such as a bed, a mat, a blanket, a bed sheet, a quilt cover, and the like, because fluctuation quantity of polarized wave conditions of light propagated in the optical fiber, which is brought about by living body activities and respiration, heart beat and pulse, and like, of a human body can be detected in real time. Furthermore, sensitivity can be upgraded by raising the ratio of the detected value and noise.

BRIEF DESCRIPTION OF THE DRAWINGS

FIG. 15 is a drawing showing a relationship between living body activities of a test subject and a polarized wave fluctuation quantity $\beta$, a degree of polarized light (DOP), and the like.

LIST OF REFERENCE NUMERALS AND CHARACTERS

Figure 1:
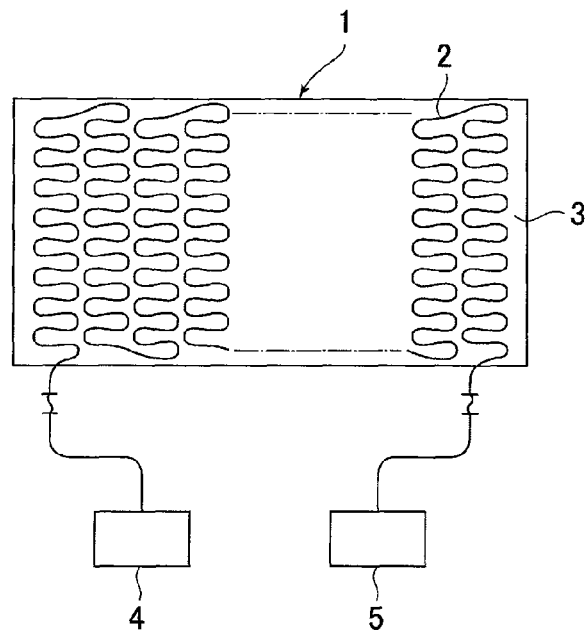
FIG. 1 is an schematic drawing showing an embodiment employed in a method for monitoring living body activities.

H Human
1 Optical fiber type flat shaped body sensor
2 Optical fiber
3 Cloth made sheet (flat shaped body)
4 Light source apparatus
5 Measuring apparatus for measuring polarized wave fluctuations
6 Floor
7 Bed
8 Mat
9 Pad
10 Cloth made sheet
11 Blanket
12 Polarized wave condition detection part
13 Polarized wave fluctuation quantity detection part
$S_1, S_2, S_3$ Stokes parameters
$\beta$ Polarized wave fluctuation quantity
14 Polarized wave branching element
15 Rotary polarization element
16 $\lambda/4$ plate
17 Photo receptor
18 Reflection mirror
19 Photo circulator
20 Optical fiber selector switch
21 Wavelength variable type light source
22 Wavelength separation filter
23a, 23b Filter
24 Connector part or partial reflection element
25 Pulse light source apparatus
26 Garment styled optical fiber type flat shaped body sensor

BEST MODE FOR CARRYING OUT THE INVENTION

Figure 2:
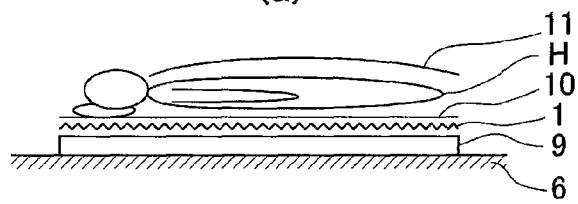
FIG. 2 is an explanatory drawing showing an example of how an optical fiber type flat shaped body sensor may be used, wherein (a) designates when the optical fiber type flat shaped body sensor is used on a floor top, (b) designates when the sensor is used on a bed, and (c) designates when the sensor is used as a top cover for a person.
Figure 2:
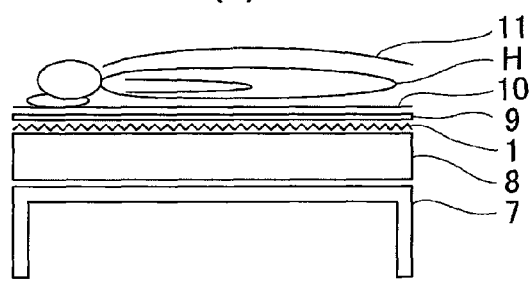
Figure 2:
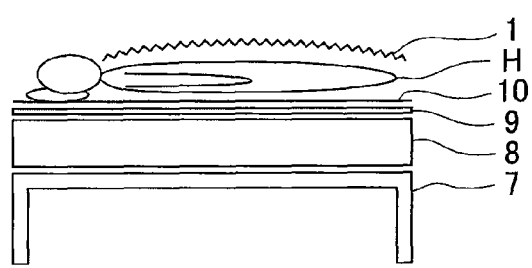

Preferred embodiments in accordance with the present invention are described as follows with reference to the drawings. FIG. 1 is an explanatory drawing showing an embodiment employed in a method for monitoring living body activities (i.e., respirations, heart pulsation, movement) in accordance with the present invention. FIG. 2 is an explanatory drawing showing examples of uses of an optical fiber type flat shaped body sensor in accordance with the present invention.

With reference to FIG. 1, 1 designates an optical fiber type flat shaped body sensor, 2 designates an optical fiber, 3 designates a cloth made sheet (flat shaped body), 4 designates a light source apparatus, and 5 designates a measuring apparatus for measuring polarized wave fluctuations. With reference to FIG. 2, 6 designates a floor, 7 designates a bed, 8 designates a mat, 9 designates a pad, 10 designates a cloth made sheet (i.e., a cloth such as a sheet), 11 designates a blanket and H designates a human.

The aforementioned optical fiber type flat shaped body sensor 1 is made with an optical fiber 2 that is fixed to the entire surface of a cloth sheet 2. As described later, there exist a variety of structures, forms and methods of fixing the optical fiber 2 to be used in constructing the optical fiber type flat shaped body sensor 1.

As shown in FIG. 2, the optical type flat shaped body sensor 1 is used by fitting it on the top of a bed 7 or a floor 6, or in the form of a blanket so as to cover a human H with the optical type flat shaped body sensor 1. Also, as described later, it is possible that the optical fiber type flat shaped body sensor 1 is not only used in the form of a sheet or a spread, but it also may be used in the form of a pillow case, or a cover sheet for a Futon-mat, or in the form of a pajama, night wear, underwear, and the like.

Figure 3:
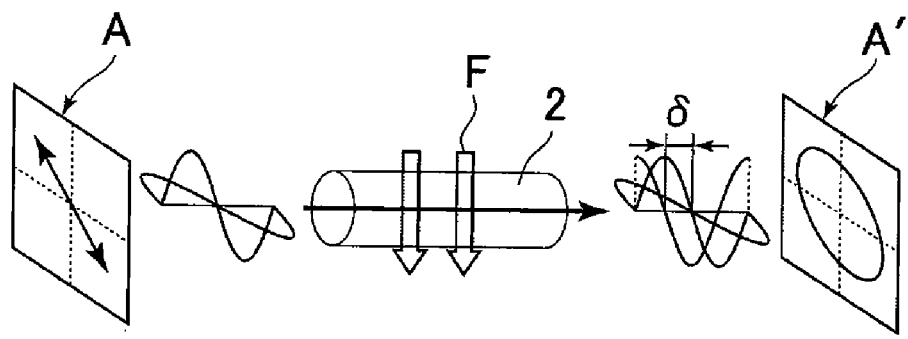
FIG. 3 is an explanatory drawing showing polarized wave fluctuations of light passing through an optical fiber wherein (a) shows polarized wave conditions of the plane of emission (to be ellipse-shaped) when stress (F) is applied, (b) shows deformed conditions of an optical fiber 2 caused by living body activities of a human, and (c) illustrates a relative relationship between the direction of vibration and stress F that bring about the maximum polarized wave fluctuations and the form of the optical fiber 2, respectively.
Figure 3:
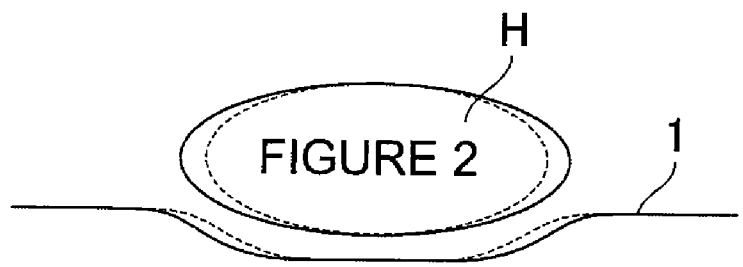
Figure 3:
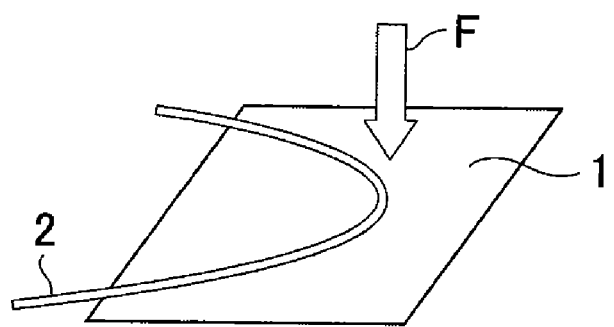

As evident from FIGS. 1 and 3(b), a method for monitoring living body activities, in accordance with the present invention, is based on the fact that when stress, such as vibration, pressure or the like, brought about by living body activities (getting into bed, getting out of bed, respiration, heart or artery pulsation, and the like) of a human H is applied to an optical fiber 2 of the optical fiber type flat shaped body sensor 1, then polarized wave fluctuations are brought about on light propagated in the optical fiber 2 and may be detected by the measuring apparatus 5 for measuring polarized wave fluctuations. FIGS. 3 (a), (b) and (c) is an explanatory drawing to illustrate the concept of the aforementioned polarized wave fluctuations, and FIGS. 4 (a), (b) and (c) is an explanatory drawing to show the principal structure constituting the aforementioned measuring apparatus 5 for measuring polarized wave fluctuations.

In particular, when light propagating in the optical fiber 2 is subjected to a magnetic field, pressure, vibration, temperature changes, and the like, or, for example, the optical fiber 2 is subjected to an applied stress F, as shown in FIG. 3(a), and an incident polarized wave plane A is made to be elliptic like the emitting polarized wave plane A'. The polarized wave plane mentioned here means the vibration plane of the electric field when light is taken as an electromagnetic wave, such as shown in FIG. 3 (a).

Generally, polarized wave fluctuations are detected by means of the constituent oriented only in the horizontal direction toward the emitting polarized wave plane A' such as are taken out normally using a polarizer, and changes of the polarized wave are detected as changes of light strength. However, polarized wave conditions change at random during propagation. Therefore, so that the maximum degree of modulation (strength changes) can be obtained at the emission end, it has conventionally been necessary that a polarizer and a polarized wave adjuster be rotated and adjusted for detection. In accordance with the present invention, such adjustments are not needed, and the invention is made so that stokes parameters are measured as described later.

The indication of polarized wave conditions of light wave signals is provided normally using stokes parameters $S_1$, $S_2$, $S_3$. As described later, such indication is performed using values $S_1$, $S_2$, $S_3$ (stokes parameter $S_1$ is a linear polarized wave in a horizontal⇔vertical direction, stokes parameter $S_2$ is a linear polarized wave in a +45 degree⇔−45 degree direction, and stokes parameter $S_3$ is a circular polarized wave of a right turn ⇔ a left turn) corresponding to each light strength constituent directly measured using three kinds of polarized filters on Poincaré's spherical surface.

FIGS. 3(a) and (b) show the relationship between the direction stress F applied to the optical fiber 2 and the width of polarized wave fluctuations. Empirically it has been found that polarized wave fluctuations, brought about by vibration or bend force F applied to optical fiber 2, have been dependent largely on the form (shape) of the optical fiber. In other words, polarized wave fluctuations are found to be relatively large when vibration is applied in a perpendicular direction to the original bent or curved face of the optical fiber 2.

Figure 4:
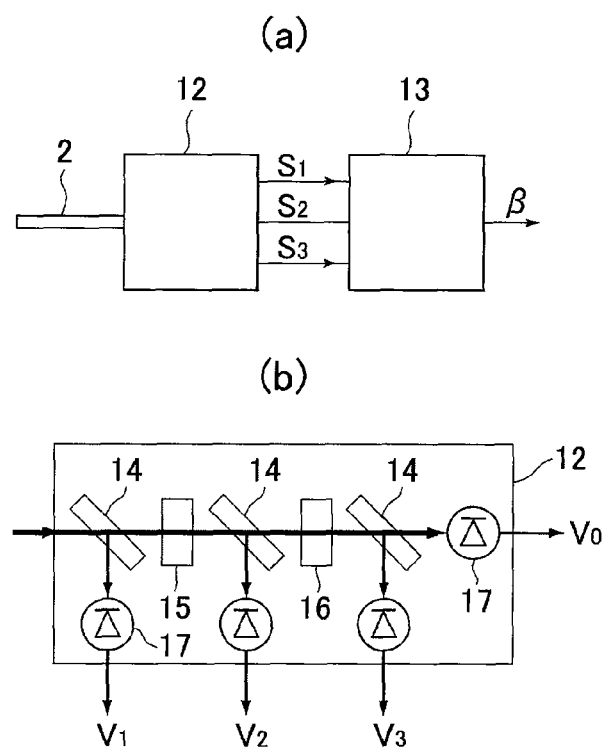
FIG. 4 is an explanatory drawing of a measuring apparatus 5 for measuring polarized wave fluctuations wherein (a) is an explanatory drawing of an entire basic constitution of the measuring apparatus, (b) is an explanatory drawing of the basic constitution of a polarized wave condition detection part, and (c) is an explanatory drawing showing how the polarized wave condition detection part and a polarized wave fluctuation quantity detection part are connected.
Figure 12:
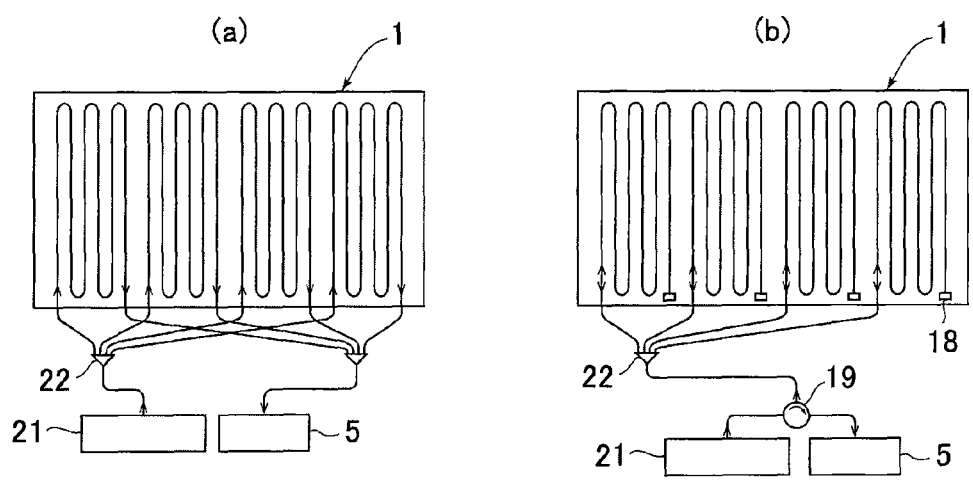
FIG. 12 is an explanatory drawing illustrating still other embodiments (a) and (b) employed in a method for monitoring living body activities.

FIG. 4 is a schematic drawing showing the basic configuration of a measuring device 5 for measuring polarized wave fluctuations in accordance with the present invention. With reference to FIG. 4(a), 12 designates a polarized wave condition detection part, 13 designates a polarized wave fluctuation quantity detection part, and β designates a polarized wave fluctuation quantity that has been detected.

FIG. 4(b) illustrates an example of the basic configuration of an element incorporated into the polarized wave condition detection part 12, wherein 14 designates a polarized light branching element, 15 designates a rotary polarization element, 16 designates a λ/4 plate and 17 designates a photo receptor. The aforementioned polarized light branching element 14 is an element that is used to take out a horizontal polarized light constituent at the branching ratio of approximately 1~5%. The rotary polarization element 15 is made so that the plane of the polarized light is rotated by 45 degrees. Furthermore, the λ/4 plate is made so that a doubly refracting principal axis thereof is set at 45 degrees from the horizontal face or plane.

Generally, it is required, as mentioned above, that a vibration-centered position on the sphere and the direction of vibration be adjusted in order to detect polarized wave fluctuations with high sensitivity. However, it is not easy to make such necessary adjustments in a short period of time. Thus, in accordance with the present invention, the polarized wave fluctuation quantity detection part is made so that the polarized wave fluctuation quantity β is computed using three constituents of the polarized wave, namely, $S_1$, $S_2$, and $S_3$.

In particular, output signals $V_1$, $V_2$, $V_3$, $V_0$ of each photo receptor 17 are corrected for sensitivity differences using a light branching element and the like (that is, correction is made so that $V_1$, $V_2$, and $V_3$ become the values of $0 \sim V_0$ depending on polarized wave conditions). Thus, the polarized wave fluctuation quantity β is computed using stokes parameters $S_1$, $S_2$, $S_3$ obtained as $Sj=2Vj/V_0-1$ (where $j=1,2,3$).

Figure 5:
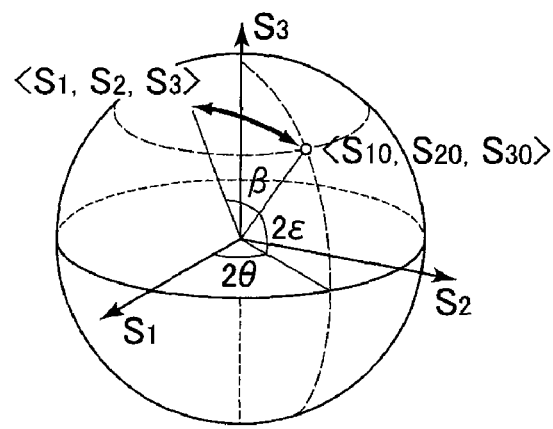
FIG. 5 illustrates definitions of the display of polarized wave fluctuations and a polarized wave fluctuation quantity with a stokes parameter detected by the polarized wave condition detection part of the measuring apparatus for polarized wave fluctuations, respectively.

Specifically, as shown in FIG. 5, standard conditions of polarized wave fluctuations are set as $S_{10}$, $S_{20}$, $S_{30}$. Assuming stokes parameters, which show polarized wave conditions as measured, are $S_1$, $S_2$, $S_3$, then the triangle with 2 vertices [$V_1$, $V_2$, $V_3$] [$S_{10}$, $S_{20}$, $S_{30}$] and the origin [0, 0, 0] becomes an isosceles triangle as shown in FIG. 5, and its vertex angle β is expressed by the following equations:

$$\beta = 2\sin^{-1}(dL/2) \tag{1}$$

$$dL = \sqrt{(dS_1^2 + dS_2^2 + dS_3^2)} \tag{2}$$

$$dSj = Sj - Sj_0 \tag{3}$$

(where j=1,2,3)
In accordance with the present invention, the angle β is defined as a polarized wave fluctuation quantity. In this case, dsj is defined as the change quantities of each coordinate, and dL is equivalent to the travel distance of a coordinate point. The distance from the coordinate original point to a coordinate point is defined as the degree of polarized light (DOP=$S_1+S_2+S_3$). However, in the case that monochromatic light is used, it is that DOP=1. Here, the abbreviation "DOP" stands for "degree of polarized light." With reference to FIG. 5, θ is a so-called polarized wave principal axis azimuth, and ε is an elliptic rate angle.

The polarized wave fluctuation quantity β, expressed by equation (1) shown above, is computed in real time using the polarized wave fluctuation quantity detection part 13 shown in FIG. 4(a) without making so-called polarized wave adjustments. The polarized wave fluctuation quantity detection part 13 is constituted as a digital (or analogue) type computation apparatus.

Figure 4C:
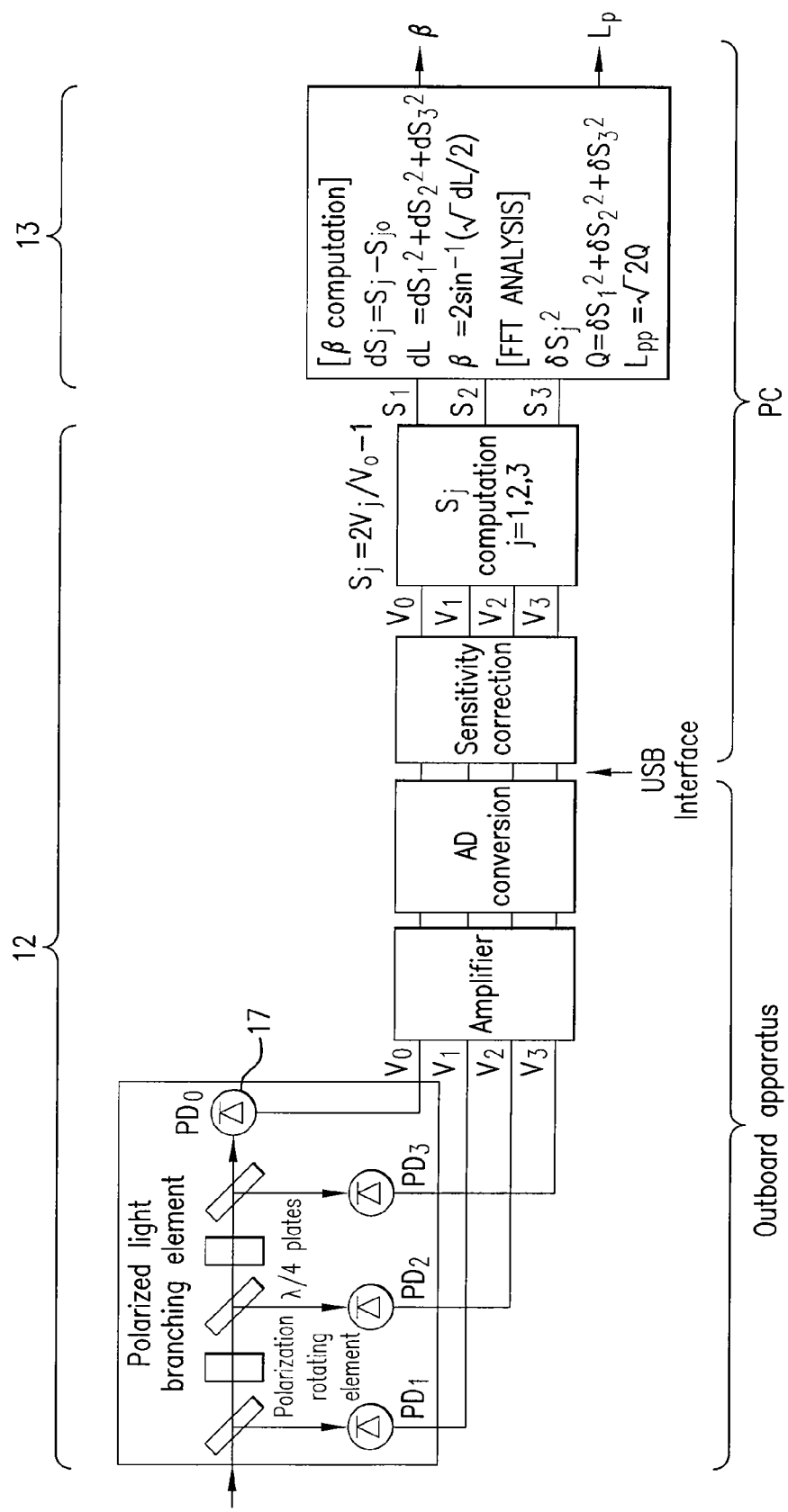

Specifically, as shown in FIG. 4(c), light is converted to electric signals by each photo receptor 17, amplified using a log amplifier, AD-converted and transmitted to a PC (personal computer) via mediation of the USB interface. On the PC side, stokes parameters $S_1$, $S_2$, $S_3$, the degree of polarized light (DOP) and the polarized wave fluctuation quantity β are computed by the personal computer PC, and the computed results are stored on a hard disc together with data pertaining to the strength of light, time data, and key events (i.e., key entry of condition changes and the like for outputting as a memo or report). The range of the log amplifier is 30 dB, the resolving power of the AD converter is 12 bit (value of 1500 per digit) and the velocity is 10 kHz. The transmission period of the USB is 0.01 sec. The system shown in FIG. 4(c) is constituted so that an average is obtained for every 10 data units; thus, computation and storage is performed with periodicity of 0.1 sec after making the average for every 10 data units.

The aforementioned polarized wave fluctuation quantity detection part 13, shown in FIG. 4, is constituted so that the polarized wave fluctuation quantity β is computed using equations (1), (2), (3) above by using the stokes parameters $S_1$, $S_2$, $S_3$. However, as is discussed below, in the case where a survey is conducted on contents of feeble vibration (for example, feeble and periodic vibration wave forms such as those produced by respiration and pulse or heart beat of a human), it is believed that feeble vibration can be more easily discriminated using the wave forms of stokes parameters $S_1$, $S_2$, $S_3$ than using the polarized wave fluctuation quantity β. Thus, a FFT (Fast Fourier Transform) analysis of the stokes parameters is conducted to determine the vibration detection limit, and based on the results improvements in detection sensitivity are achieved by setting a standard for the polarized wave fluctuation quantity β and by performing a moving average treatment or computation.

As shown in FIG. 5 and the like, the aforementioned polarized wave fluctuations are expressed by vibration on the spherical surface of a radius of 1 wherein stokes parameters $S_1$, $S_2$, $S_3$ are expressed by the 3-dimensional orthogonal coordinates of x, y, z, and the polarized wave fluctuation quantity β is expressed by the equations (1) to (3) discussed above.

To obtain the fluctuation width (peak to peak) of periodic vibration, both vibration peaks (i.e., maximum and minimum peaks of the wave train) can be replaced with S1, S2, S3 and S10, S20, S30 as shown in FIG. 5. That is, in the case of feeble vibration, equation (1) becomes as:

$$\beta p \cdot p = dL [\text{rad}] \tag{4}$$

(in the case of [degree] unit, $dL*180/\pi$)
Now, in the case of vibration of single frequency F, assuming that the vibration widths of the stokes parameters are $dS_{1f}$, $dS_{2f}$, $dS_{3f}$ when there exists no phase difference between the vibration of the stokes parameters, equation (2) can be written as:

$$dL_f^2 = dS_{1f}^2 + dS_{2f}^2 + dS_{3f}^2 \tag{5}$$

Here, ½ of $dS_{jf}^2$ (j=1,2,3) is equivalent to a vibration power with a frequency f of Sj. Therefore, the power spectrum can be obtained by performing the aforementioned FFT on the three wave forms of the measured stokes parameters S1, S2, S3, thus making it possible to achieve evaluation thereof using the total value.

In particular, the power spectrum can be obtained by treating the three stokes parameters $S_1$, $S_2$, $S_3$ with FFT, and the power spectrum's total Q is obtained as $Q=\zeta S_1^2+\zeta S_2^2+\zeta S_3^2$, and the amplitude Lpp of the frequency constituent of the vibration peak is obtained as Lpp=$\sqrt{(2\ Q)}$. The theory or concept of analysis by FFT is substantially the same as that of the analysis of the polarized wave fluctuation quantity β demonstrated in accordance with equations (1) to (3) as discussed above. Because polarized wave fluctuation quantity β is computed using the difference between stokes parameters at the present time and the stokes parameters at a time antecedent to a specified time (i.e., a standard value), detection of fluctuations can be easily performed, and an instantaneous response property or characteristic (i.e., a real time property or characteristic) is found to be excellent. However, when the time span for measuring employed for computation purposes is too short for a comparatively slow vibration, the polarized wave fluctuation quantity β becomes obscured by noise for the reason that the width of the changes of the stokes parameters caused by vibration becomes smaller than the width of the noise.

For example, in the case of an artery or heart pulsation waveform, which is described later, the existence of vibration can be identified when the entire waveform is detected, but it will be difficult to appreciate instantaneous changes using the difference between after- and before-samplings when the entire waveform is not detected. Furthermore, in order to raise the signal and noise ratio SNR of the polarized wave fluctuation quantity β, it is required that (a) a moving average treatment (n) of the stokes parameters be optimized, and (b) that the time width (m) for computing β be optimized. To do so, the following two treatments or processes are conducted in accordance with the present invention.

a. For optimization of a moving average treatment of stokes parameters, the k-th sampling data, Sj(k)(j=1,2,3), of the stokes parameters are transformed to the averaged Sj(k)a when the number of the moving average=n is as provided below by:

$$Sj(k)a = (1/n)* \sum_{i=0}^{n-1} Sj(k-i) \tag{6}$$

In accordance with the present invention, n=1 corresponds to the case of (Sj(k)a=Sj(k)) without the stokes parameters being averaged.

b. Next, treatment for optimization of the time width for the polarized wave fluctuation quantity β, when the computation width of β is obtained using equations (1) to (3), β(k) obtained by the k-th data Sj(k) is made to be the standard for the stokes parameters antecedent to the m sample from those stokes parameters of the present time, and equation (3) is replaced as follows below:

$$dSj(k)=Sj(k)-Sj(k-m).$$

Here, Sj(k) can be Sj(k)a averaged with a.

Figure 6:
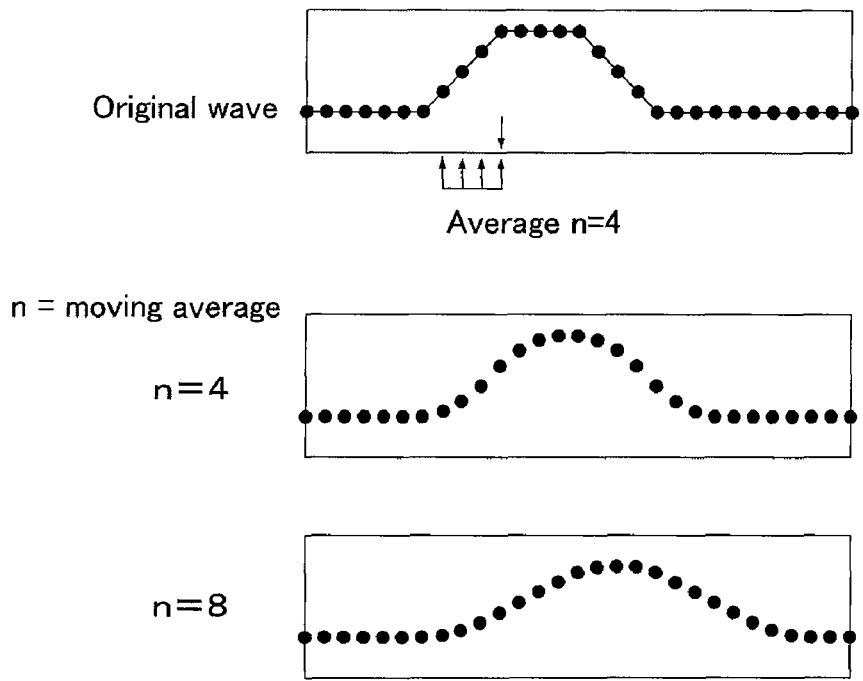
FIG. 6 is an explanatory drawing to illustrate the concept of a moving average treatment of a polarized wave fluctuation quantity $\beta$.
Figure 7:
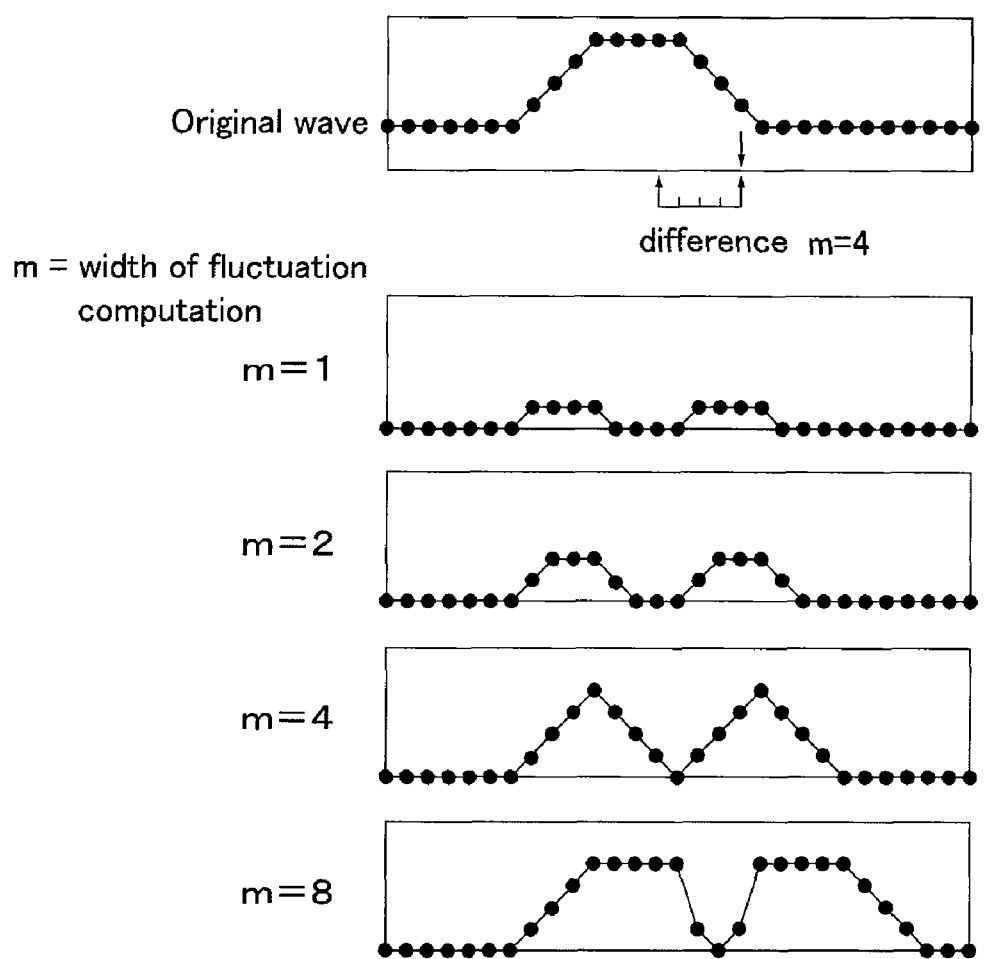
FIG. 7 is an explanatory drawing to illustrating the concept of a fluctuation computation width treatment of a polarized wave fluctuation quantity $\beta$.

FIG. 6 and FIG. 7 are explanatory drawings of the aforementioned moving average treatment and the fluctuation quantity computation width treatment. As apparent from FIG. 6, in accordance with the moving average treatment, a rise time is delayed by the moving average number n, and the signal peak becomes smoother or is smoothened. Thus, the signal peak becomes small when the moving average number n is excessive. However, the fluctuation quantity computation width m is not affected by this effect. Consequently, there is no delay with respect to the rise time and the peak does not become small when the fluctuation quantity computation width m is excessive. However, when an original waveform is observed as a periodic vibration as shown in FIG. 7, a delay is caused by the fluctuation quantity computation width m, and the waveform is disrupted in the case when fluctuation quantity computation width m is excessive. When the fluctuation quantity computation width m is small, the amplitude of the periodic vibration thus observed becomes smaller than the original waveform, thus creating the possibility that it will be buried by noise.

Accordingly, it is recommended that the moving average number n and the average computation width m be set to be shorter than ½ the assumed vibration periodicities. In accordance with this embodiment of the present invention, the sampling periodicity is 0.1 sec/sample, and the effectiveness will be less than 25 sample respirations if the vibration periodicity of respiration is approximately 5 sec.

Illustrative Embodiment 1

FIGS. 8(a) to FIG. 8(d) show preferred embodiments of the optical fiber type flat shaped body sensor 1 in accordance with the present invention. As shown in FIG. 3(b) and FIG. 3(c), polarized wave fluctuations caused by vibration and bend stress F applied to the optical fiber 2 become relatively large when vibration and the like are applied in the direction perpendicular to the original bend plane of the optical fiber 2. Therefore, 4 different types of sensors 8(a) to 8(d) have been constructed.

The optical fiber 2 is affixed to a cloth made sheet 3 (i.e., a flat shaped body consisting of a cloth such as a sheet). The optical fiber is constituted in this case as a single mode optical fiber 2 with a covered outer diameter of approximately 0.5 mm and a conductor clad, which has a diameter of 0.125 mm φ. The optical fiber 2 is fixed with a synthetic resin made adhesive to the flat shaped body 3 made of blended cloth, which is a cloth made of a synthetic resin and a natural fabric blend.

Affixation of the optical fiber 2 to the flat shaped body (a cloth made sheet 3) can be achieved using any suitable method, such as by being sewed into the cloth made sheet or being caught between 2 thin cloth made sheets. The optical fiber 2 used can be bare. However, it goes without saying that the outer surface of the optical fiber 2 can be thinly covered by a covering. Furthermore, affixation of the optical fiber 2 to the cloth made sheet 3 forms flat shapes in a state of adhesion and can be of any form such as a loop shape (See FIG. 8(c)), a wave shape (See FIG. 8(d)), or any other types of shapes (See, e.g., FIG. 8(a) and FIG. 8(b)).

As is evident from the discussion of FIGS. 3(a) to 3(c), optical fiber type flat shaped body sensor 1 is flexible and may be moved from one shape or form to another shape or form by movement of a human. Movement of the optical fiber 2 in the sensor 1 is likewise caused by the human movement and may be feeble or not. When the optical fiber 2 moves due to human movement, polarized wave fluctuations with respect to the light passing through the optical fiber are produced, and these fluctuations are detected by the measuring apparatus 5 for measuring polarized wave fluctuations.

Illustrative Embodiment 2

Figure 8:
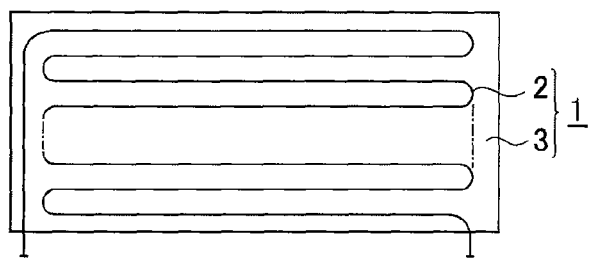
FIG. 8 is a plan view illustrating a first embodiment of an optical fiber type flat shaped body sensor, wherein (a) to (d) represent different variations of the first embodiment.
Figure 8:
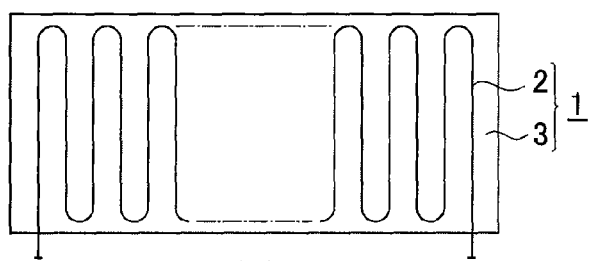
Figure 8:
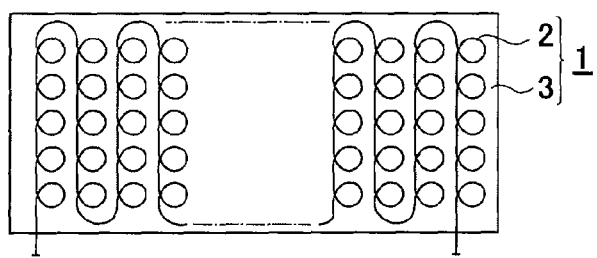
Figure 8:
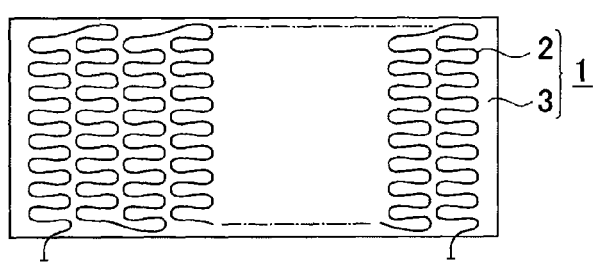
Figure 9:
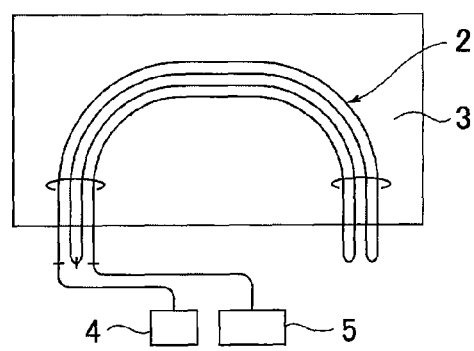
FIG. 9 is an explanatory drawing illustrating a second embodiment of an optical fiber type flat shaped body sensor.

FIG. 9 shows a preferred embodiment in the event that the structure of the optical fiber 2 shown in FIG. 8 is made to be a multi-conductor type (the number of conductors is n) optical fiber, with which improved sensitivity is brought about by polarized wave fluctuations produced due to changes in the shape (form) of the flat shaped body sensor 1. In this embodiment, a light source apparatus 4 and a measuring apparatus 5 for measuring polarized wave fluctuations are connected with the end part of one side of the multi-conductor type optical fiber 2.

Illustrative Embodiment 3

Figure 10:
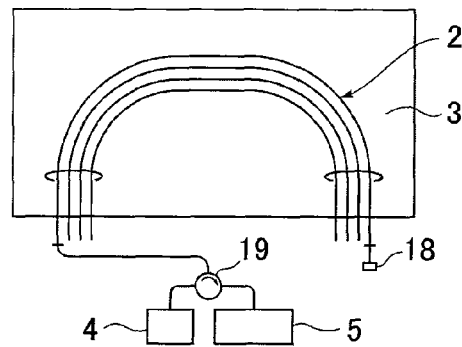
FIG. 10 is an explanatory drawing illustrating a third embodiment of an optical fiber type flat shaped body sensor.

FIG. 10 illustrates a method of raising polarized wave fluctuation sensitivity brought about by producing polarized wave fluctuations due to changes in the shapes of the flat shaped body sensor 1. Sensitivity is raised by means of a reflection mirror 18 installed at the end part of one side of the optical fiber 2 in order that light wave signals are transmitted to and fro. In accordance with FIG. 10, 19 designates an optical circulator. An optical coupler can be used as a substitute for the optical circulator 19.

Illustrative Embodiment 4

In accordance with Illustrative Embodiments 1 to 3 of the invention, the flat shaped body sensor 1 may be formed in a quadrangle shaped sheet (another flat shaped body) in accordance with yet another embodiment of the present invention. Furthermore, it goes without saying that the flat shaped body sensor 1 can be utilized, in accordance with the present invention, by means of the cloth sheet being integrally processed to make a cover for a Futon-bed, a quilt, a mat, a sofa, and the like. Also, it goes without saying that the flat shaped body sensor 1 of Illustrative Embodiment 1 to Embodiment 3 can be made watertight by using a vinyl cover. Furthermore, using the flat shaped body sensor 1 of Illustrative Embodiment 1 to Embodiment 3 to form clothes, such as pajamas or night wear, is within the scope of the present invention. Also, the optical fiber 2 can be adhered to clothes that are separately prepared (i.e., the optical fiber is adhered to cloth forming clothes instead of a sheet) in order to make a garment styled optical fiber type sensor with which any changes of the shape of the human body due to movement, respirations, pulsations, and the like can be detected as changes of the shape of the optical fiber 2.

In addition, by sewing the optical fiber 2 in a body shaped pad made in a manner so that it fits directly to the outer surface of a human body, it becomes possible to make a human body fitted optical fiber type sensor that allows any changes of the form of the pad fitted to the human body to be detected due to changes of the shape or form of the optical fiber sewn into the body shaped pad. In other words, movement or pulsation of the human body causing deforming changes in the shape of the pad fitted to the human body causes corresponding movement or changes in the optical fiber, which produces polarized wave fluctuations with respect to the light passing through the optical fiber, and these fluctuations are detected by the measuring apparatus 5 for measuring polarized wave fluctuations.

Illustrative Embodiment 5

Figure 11:
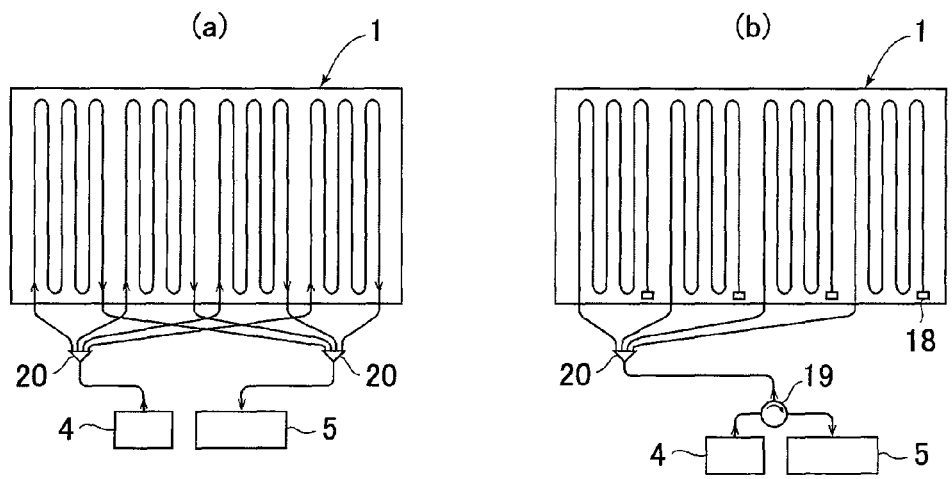
FIG. 11 is an explanatory drawing illustrating other embodiments (a) and (b) employed in a method for monitoring living body activities.

FIG. 11 shows another embodiment in accordance with the present invention wherein, by using the measuring apparatus 5 for measuring polarized wave fluctuations, a plurality of optical fiber type flat shaped body sensors, or a plurality of blocks in an optical fiber type flat shaped body sensor, can be monitored in sequence using an optical fiber selector switch 20. FIG. 11(*a*) and FIG. 11(*b*) illustrate embodiments formed as a transmittance type device and as a reflectance type device, respectively. Referring to FIG. 11(*b*), 19 designates an optical circulator.

Illustrative Embodiment 6

FIG. 12(*a*) and FIG. 12(*b*) are other preferred embodiments, in accordance with the present invention, illustrating a method for monitoring living body activities, wherein the light source apparatus 4 is a wavelength variable type light source 21, and a wavelength separation filter 22 is used as a substitute for the optical fiber selector switch 20 so that using one set of the measuring apparatus 5 for measuring polarized wave fluctuations, the polarized wave fluctuations of a plurality of optical fiber type flat shaped body sensors 1 can be detected in sequence, or the polarized wave fluctuations of a plurality of blocks of a flat shaped body sensor 1 can be detected individually and in sequence. FIG. 12(*a*) and FIG. 12(*b*) illustrate embodiments that are constituted as a transmittance type device and as a reflectance type device, respectively.

Illustrative Embodiment 7

Figure 13:
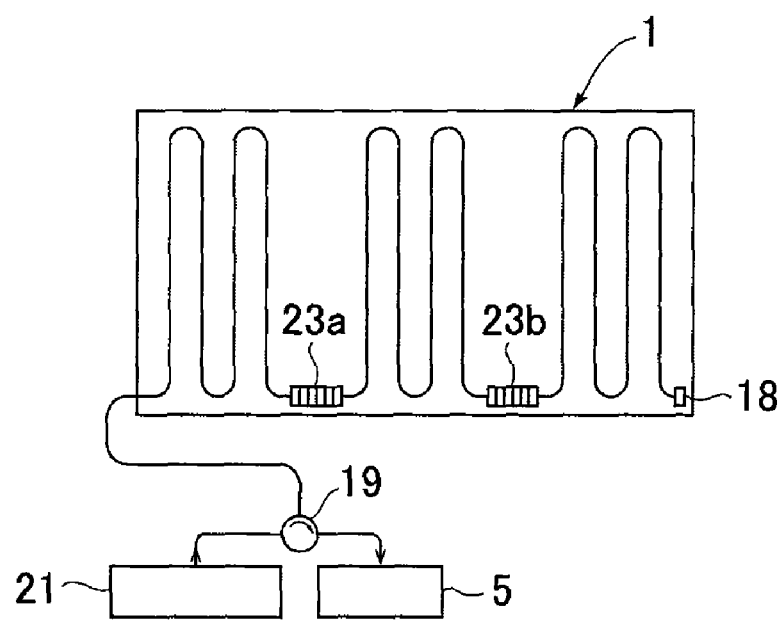
FIG. 13 is an explanatory drawing illustrating yet another embodiment employed in a method for monitoring living body activities.

FIG. 13 illustrates a preferred embodiment of another method for monitoring living body activities in accordance with the present invention, wherein a plurality of filters 23*a* and 23*b*, such as an optical fiber diffraction grating, are employed thereby allowing only a certain wavelength to reflect. The filters 23*a*, 23*b* are incorporated at some midpoint in the optical fiber 2, which makes it possible to individually discriminate and monitor a specific block of the optical fiber 2.

Illustrative Embodiment 8

Figure 14:
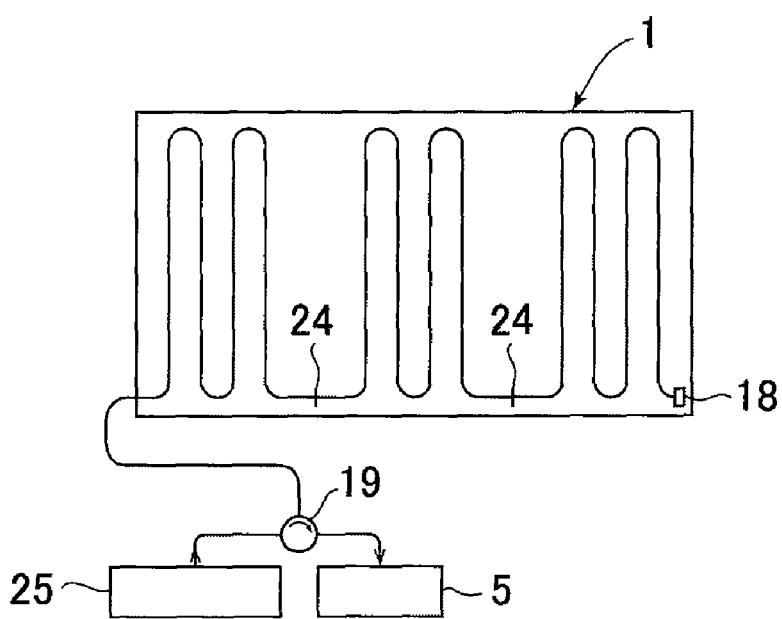
FIG. 14 is an explanatory drawing illustrating still another embodiment employed in a method for monitoring living body activities.

With reference to FIG. 14, another embodiment in accordance with the present invention is constituted so that a plurality of connectors or partial reflection elements 24 are installed at some midpoint in the optical fiber 2, and so that photo pulse signals are transmitted from a pulse light source apparatus 25. This structure makes it possible to discriminate and monitor a plurality of blocks of the optical fiber 2 in accordance with the delay time of dispersed light in the optical fiber 2. In accordance with the aforementioned Illustrative Embodiment 1 to Embodiment 8, the present embodiment of the invention may be constituted so that the light source apparatus 25 or the measuring apparatus 5 for measuring polarized wave fluctuations is directly connected to the optical fiber type flat shaped body sensor 1. However, in the case wherein the flat shaped body sensor 1 and the measuring apparatus 5, and the like, are separated over a long distance, it is possible that the flat shaped body sensor 1 is constituted by, or includes, a general communications purpose optical fiber so that the flat shaped body sensor 1 and the measuring apparatus 5 for measuring polarized wave fluctuations, and the like, are directly connected through mediation of the communications purpose optical fiber.

Illustrative Embodiment 9

TABLE 1

Measurement Test Conditions of Polarized Wave Fluctuation Quantity

| | | Flat shaped body sensor (Sheet type) | | Conditions for light transmission | |
|---|---|---|---|---|---|
| | Test case name | Type | Usage pattern | Number of conductors in use | Light direction |
| 1 | W401 | FIG. 8 (d) | FIG. 2 (a) | 4 | 1 way |
| 2 | W101 | FIG. 8 (d) | " | 1 | 1 way |
| 3 | L401 | FIG. 8 (c) | " | 4 | 1 way |
| 4 | L101 | FIG. 8 (c) | " | 1 | 1 way |
| 5 | L102 | FIG. 8 (c) | " | 1 | Reflection |

TABLE 2

Results of Assessment by Direct Visual Check on Measured Data *

| | Test case name | Strength of photo reception [mW] | Actions | | | | | | |
|---|---|---|---|---|---|---|---|---|---|
| | | | Go to bed | On back at rest | Tossing & Turning | On side at rest | Tossing & Turning | On back at rest | Get out of bed | Remarks |
| 1 | W401 | 0.838 | ◉ | ○ | ◉ | ○ | ◉ | — | ◉ | |
| 2 | W101 | 2.436 | ◉ | ○ | ◉ | Δ | ◉ | Δ | ◉ | |
| 3 | L401 | 0.117 | ◉ | X | ◉ | Δ | ◉ | X | ◉ | Big loss |
| 4 | L101 | 1.538 | ◉ | X | ◉ | Δ | ◉ | X | ◉ | |
| 5 | L102 | 1.259 | ◉ | ○ | ◉ | ○ | ◉ | X | ◉ | |
| 6 | H401 | 0.206 | ◉ | ○ | ◉ | X | ◉ | Δ | ◉ | Big loss |
| 7 | H101 | 3.112 | ◉ | ○ | ◉ | X | ◉ | Δ | ◉ | |
| 8 | H102 | 1.613 | ◉ | ○ | ◉ | X | ◉ | ○ | ◉ | |
| 9 | V401 | 1.772 | ◉ | X | ◉ | Δ | ◉ | Δ | ◉ | |
| 10 | V101 | 2.674 | ◉ | X | ◉ | X | ◉ | X | ◉ | |
| 11 | V102 | 1.529 | ◉ | Δ | ◉ | X | ◉ | X | ◉ | |
| 15 | BV402 | 1.649 | ◉ | Δ | ◉ | X | ◉ | Δ | ◉ | |
| 16 | BV102 | 2.551 | ◉ | Δ | ◉ | X | ◉ | X | ◉ | |
| 17 | BW401 | 1.245 | ◉ | ○ | ◉ | ○ | ◉ | ○ | ◉ | |
| 18 | BW101 | 2.903 | ◉ | ○ | ◉ | ○ | ◉ | ○ | ◉ | |

| | | | Respiration | | | | | | |
|---|---|---|---|---|---|---|---|---|---|
| | | | Respiration | Halt | Deep Respiration | Halt | Intense Respiration | Halt | — | Remarks |
| 19 | KW401 | 1.103 | ◉ | Δ | ◉ | Δ | ◉ | Δ | — | |

* Existence of meaningful vibrations
◉ Clearly seen
○ Slightly seen
Δ Difficult to judge
X Not seen

TABLE 1-continued

Measurement Test Conditions of Polarized Wave Fluctuation Quantity

| | | Flat shaped body sensor (Sheet type) | | Conditions for light transmission | |
|---|---|---|---|---|---|
| | Test case name | Type | Usage pattern | Number of conductors in use | Light direction |
| 6 | H401 | FIG. 8 (b) | " | 4 | 1 way |
| 7 | H101 | FIG. 8 (b) | " | 1 | 1 way |
| 8 | H102 | FIG. 8 (b) | " | 1 | Reflection |
| 9 | V401 | FIG. 8 (a) | " | 4 | 1 way |
| 10 | V101 | FIG. 8 (a) | " | 1 | 1 way |
| 11 | V102 | FIG. 8 (a) | " | 1 | Reflection |
| 15 | BV402 | FIG. 8 (a) | FIG. 2 (b) | 4 | 1 way |
| 16 | BV102 | FIG. 8 (a) | " | 1 | 1 way |
| 17 | BW401 | FIG. 8 (d) | " | 4 | 1 way |
| 18 | BW101 | FIG. 8 (d) | " | 1 | 1 way |
| 19 | KW401 | FIG. 8 (d) | FIG. 2 (c) | 4 | 1 way |

Figure 15:
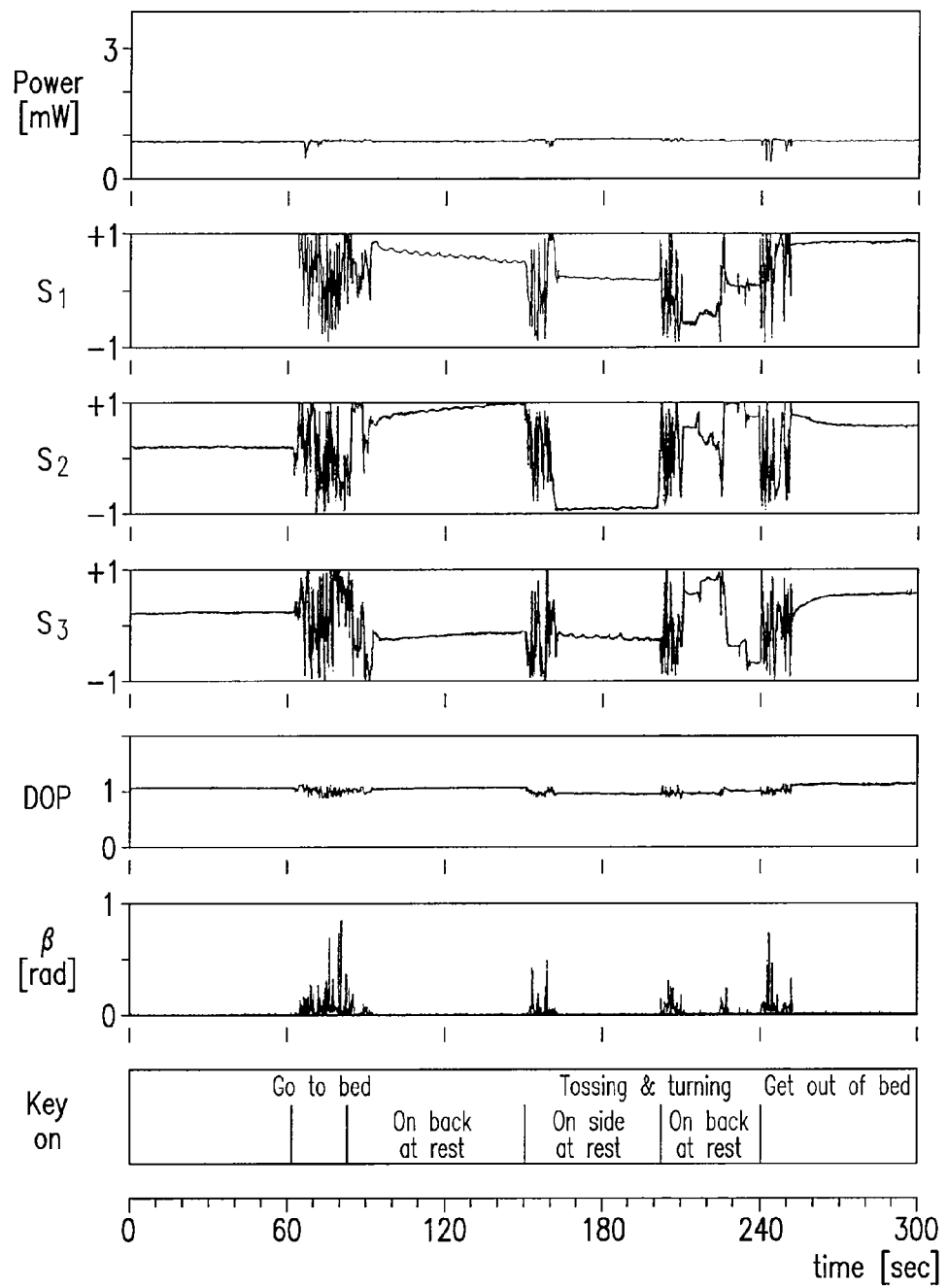

As shown in Table 1, by using an optical fiber type flat shaped body sensor 1 as shown in FIGS. 8(a), (b), (c), (d) in conditions as illustrated in FIGS. 2(a), (b), (c), measurements were conducted for monitoring activities of a test subject using a measuring apparatus for measuring polarized wave fluctuations. As described below, FIG. 15 shows measured data collected under the measurement test conditions of Test No. 1 compiled in Table 1. With respect to FIG. 15, on the vertical axis, Power represents the strength of the light employed, $S_1$, $S_2$, $S_3$ represent stokes parameters (i.e., the 3 constituents of a polarized wave), DOP represents the degree of polarized light, β represents the polarized wave fluctuation quantity, and "Key" represents key conditions documenting various human activities, respectively, From the results of the aforementioned measurements, whether or not movements of the test subject could be checked visually were judged and compiled as data. The results are shown in Table 2. Specifically, with Test No. 19 (when an optical fiber type flat shaped body sensor 1 is used instead of a cover blanket), a clear judgment was possible with respect to respiration or non-respiration of the test subject directly from the so-called raw data.

Illustrative Embodiment 10

By using the wave styled optical fiber type flat shaped body sensor 1 shown in FIG. 1 in the manner and form as shown in FIG. 2(a), an analysis was conducted on the polarized wave fluctuation quantity β obtained from a variety of living body activities of a human H (i.e., a test subject or object). FIG. 15 shows the state of activities (see "Key") of the test object (H), which can be compared over time with the stokes parameters $S_1$ to $S_3$, the degree of polarized waves (DOP), the polarized wave fluctuation quantity β, and the strength of light (Power) detected and computed by the measuring apparatus 5 for polarized wave fluctuations. From the data presented by FIG. 15, it is learned that the strength of light (Power) remains the same or constant but stokes parameters $S_1$, $S_2$, $S_3$ and the polarized wave fluctuation quantity substantially change with time corresponding to various activities of the test object. At the time of rest of the test subject, there are seen periodic changes at some points of the stokes parameters.

Figure 19:
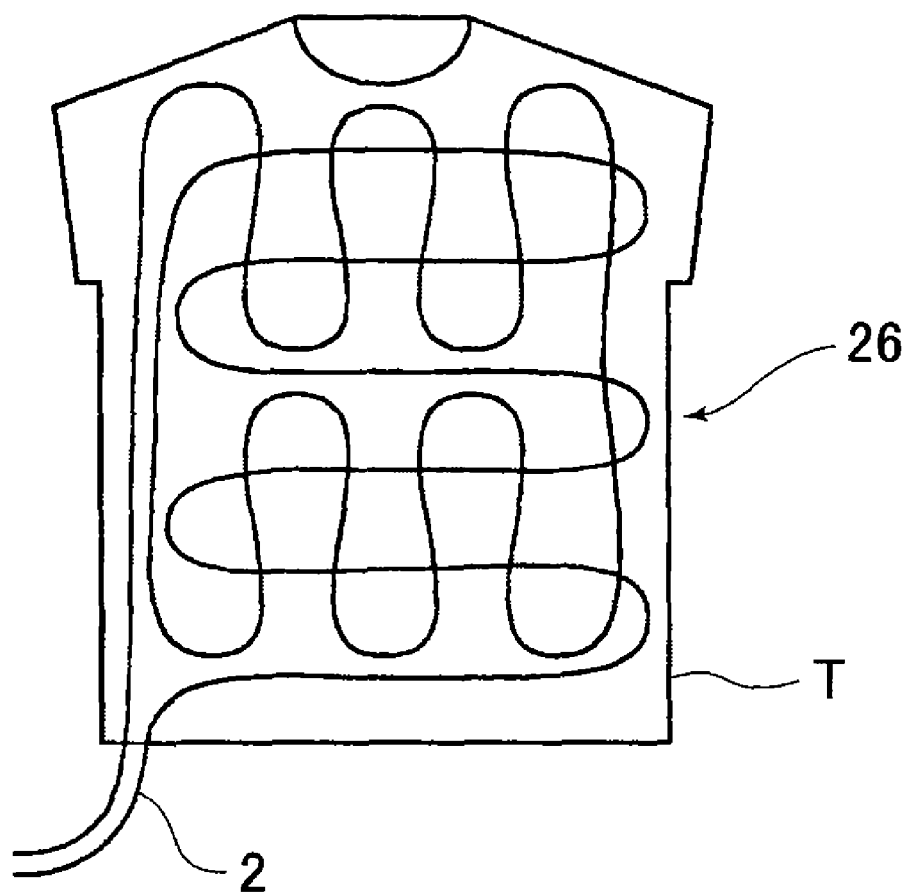
FIG. 19 is a plan view of an example of a garment styled optical fiber type flat shaped body sensor of the present invention.

The optical fiber 2 of the flat shaped body sensor 1 used for Test No. 1 is of a 4-conductor type, is as shown in FIG. 9, and its constitution is of a 2-reciprocation type. In this context a "reciprocation" pertains to how the optical fiber 2 duplicates its base pattern. Thus, as shown in FIG. 9, the optical fiber is a "2-reciprocation type." As shown in FIG. 19, the optical fiber 2 is configured to include a "3-reciprocation type" having two tiers and a horizontal "3-reciprocation type" configuration or form.

Figure 16A:
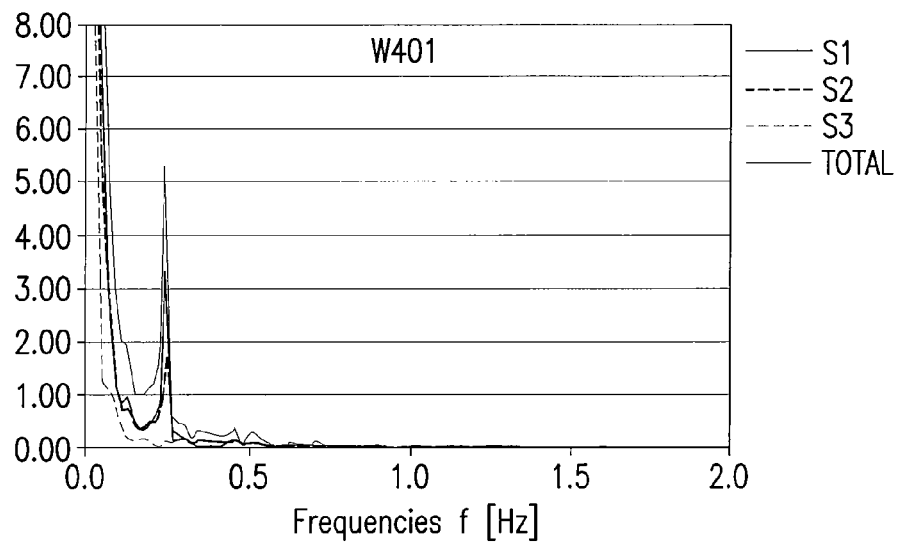
FIG. 16(a) shows the analytical results for 51.2 sec with the posture of the test subject being laid on one's back at rest, and (b) shows the analytical results for 25.6 sec with the posture of the test subject being laid on one's side at rest, respectively.
Figure 16B:
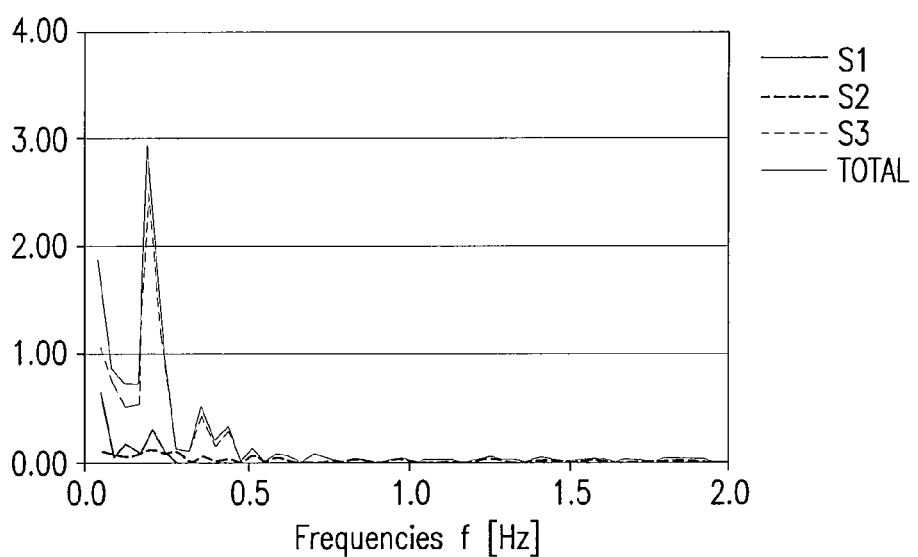
FIG. 16 graphically illustrates the results of the FFT-analysis of a stokes parameter shown in FIG. 15 by using equation (5).

FIG. 16 shows the results of the stokes parameters shown in FIG. 15 after being FFT-analyzed by using the aforementioned equation (5). FIG. 16(a) corresponds to the FFT of the stokes parameters analyzed for 51.2 seconds (sec) when the test subject laid on its back at rest, and (b) corresponds to the FFT of the stokes parameters analyzed for 25.6 sec when the test subject laid on its side at rest. The lateral axis of FIGS. 16(a) and 16(b) is for frequencies, while the longitudinal axis corresponds to the power spectrum which numeric values are made $10^4$ times (i.e., $\times 10^4$). For both FIGS. 16(a) and 16(b) a strong spectrum appeared in the vicinity of 0.2 Hz. Therefore, from this information it can be determined that this spectrum is caused by respiration.

Figure 17A:
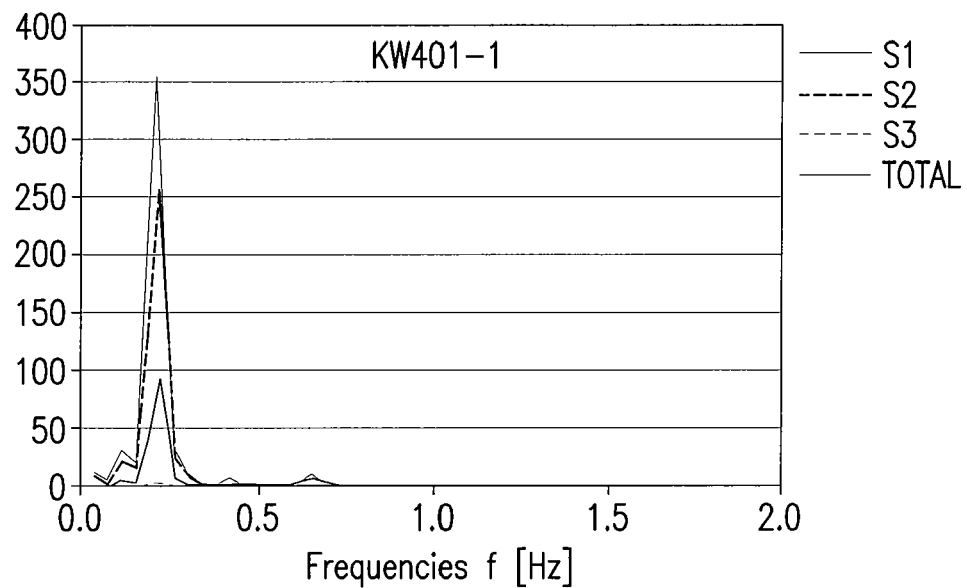
FIG. 17(a) shows the analytical results for 25.6 sec with the posture of the test subject being laid on one's back at rest under normal breathing conditions, and (b) shows the analytical results for 6.4 sec with the posture of the test subject being laid on one's side at rest under no breathing condition (no respiration).
Figure 17B:
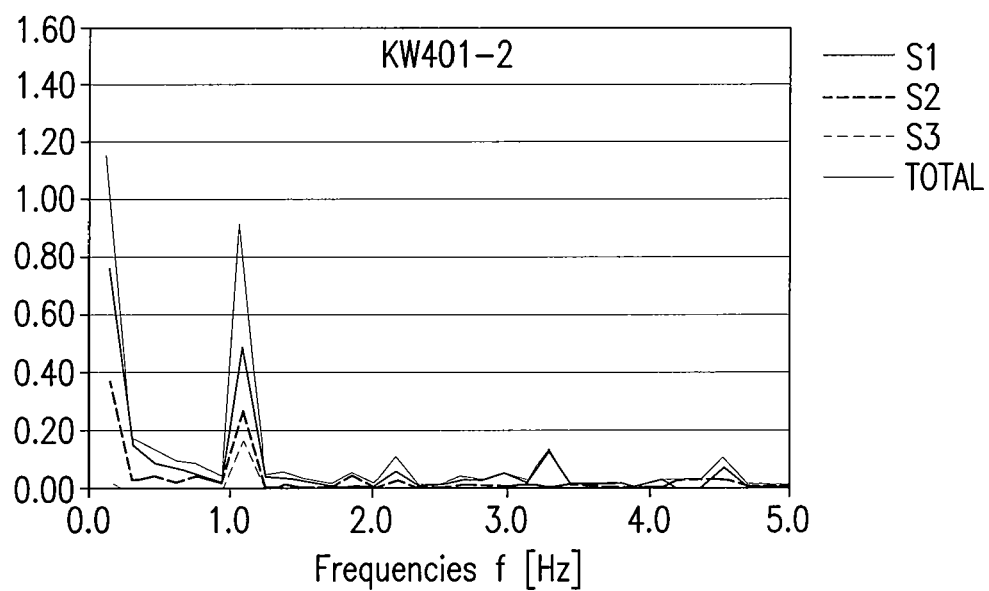
FIG. 17 graphically illustrates the results of the FFT-analysis of Test Case 19 (KW401) shown in Table 1 by using equation (5).

FIG. 17 shows the results of the test case No. 19 shown in Table 1 when FFT-analyzed using the aforementioned equation (5). FIG. 17(a) corresponds to the FFT of the stokes parameters analyzed for 25.6 sec when the test subject laid on its back at rest while breathing normally (normal respiration), and (b) for 6.4 sec when the test subject laid on its back at rest while respiration is halted (non-respiration, a state wherein the test subject is not breathing). With respect to FIG. 17 (a), an extremely strong spectrum appeared in the vicinity of 0.2 Hz, which was easily determined to be caused by respiration. On the other hand, with respect to FIG. 17 (b) it was confirmed that a spectrum peak in the vicinity of 1.1 Hz existed, which the inventors learned was caused by heart pulsation.

According to the visual assessments compiled in Table 2, polarized wave fluctuations at the time respiration was halted were too feeble to be recognized by visual inspection. However, analysis of the data collected with respect to the present invention confirmed that there existed signals corresponding to heart pulsation.

In order to detect the existence of feeble vibration and its frequencies using the aforementioned FFT analysis, the computation time required for the analysis is approximately 5 times the periodicity of the vibration of the test object (i.e., 6 sec for heart pulsation and 25.6 sec for respiration). Analysis of vibration frequencies, and the like, can not be performed using the polarized wave fluctuation quantity β directly. Instead, it is the existence of polarized fluctuations that can be detected instantaneously because the time delay in computation becomes approximately a moving average n of stokes parameters and the β computation width m.

Figure 18:
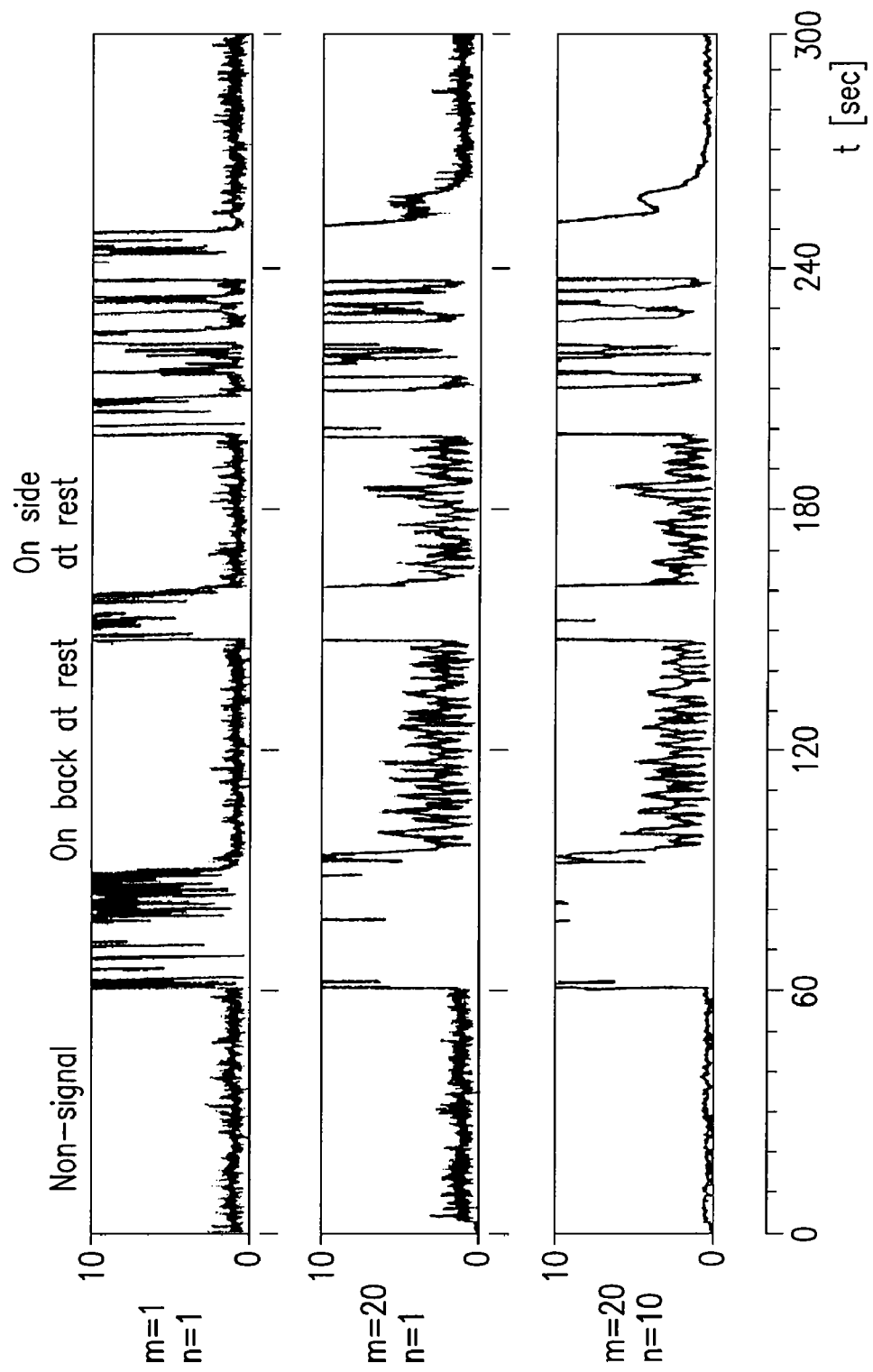
FIG. 18 shows the difference in signals when values m and n are changed by expanding a longitudinal axis so that fluctuations during the still period can be clearly seen with regard to the wave forms of the polarized wave fluctuation quantity shown in FIG. 15.

Polarized wave fluctuations shown in FIG. 18 are illustrated by a strip equivalent to the case wherein both the moving average n and the β computation width m are 1. The existence of prominent actions, such as tossing and turning, getting into bed, getting out of bed, and the like, can be instantaneously detected from the results. Furthermore, FIG. 18 shows an up-scaled (magnified) longitudinal axis of the waveform of the polarized wave fluctuation quantity β shown in FIG. 15. In the first or top strip, which illustrates the case wherein m=1 and n=1, it is difficult to identify a difference between noise occurring at the time of non-signals before the human test subject goes to bed and signals occurring after the test subject has laid on its back at rest and has laid on its side at rest in bed. In the next or middle strip, which illustrates the case wherein m=20 and n=1, noise remains unchanged at the time of non-signals occurring before the human test subject goes to bed. On the other hand, fluctuation signals distinctly appear when the test subject has laid on its back at rest and also has laid on its side at rest. In the third or bottom strip, which illustrates the case wherein m=20 and n=10, noise occurring at the time of non-signals is reduced remarkably, and signals occurring at the time when the test subject has laid on its back at rest and laid on its side at rest are clearly identifiable.

Embodiment 11

FIG. 19 is a schematic plan view of a garment styled optical fiber type flat shaped body sensor 26 in accordance with the present invention. The garment styled optical fiber type flat shaped body sensor 26 is formed in the manner that the same optical fiber 2, as the one employed by the optical fiber type flat shaped body sensor 1 shown in FIG. 1, is fitted to a T-shirt that is made from a so-called natural or synthetic fabric. More specifically, an optical fiber 2 provided with 1 conductor or 4 conductors is affixed to the outer surface of the cotton made T-shirt T. The optical fiber 2 is affixed in the shape of the combination of a wave (3-reciprocation and 2-tier) type and a horizontal (3-reciprocation) type as shown in FIG. 19.

A test was conducted wherein conditions of respiration of the test object, a male adult who wore the garment styled fiber type flat shaped body sensor 26, were changed with two (2) positions, namely sitting and lying down positions. Furthermore the test was performed, using two (2) different garment styled optical fiber type flat shaped body sensor 26, namely, one garment provided with an optical fiber having 1 conductor and the other garment provided with an optical fiber having 4 conductors. Thus, 4 different conditions of the test were evaluated in total. For the test, the pattern of respiration of the test subject was made to be a certain one applicable to all cases as follows: normal respiration (30 sec)→respiration halted (10 sec)→deep respiration (20 sec)→respiration halted (10 sec)→intense respiration (20 sec). In other words, the test subject breathed normally for 30 seconds, then halted respiration for 10 seconds, then resumed deep breathing for 20 seconds, then halted respiration a second time for 10 seconds, then breathed intensely for 20 seconds.

Figure 20:
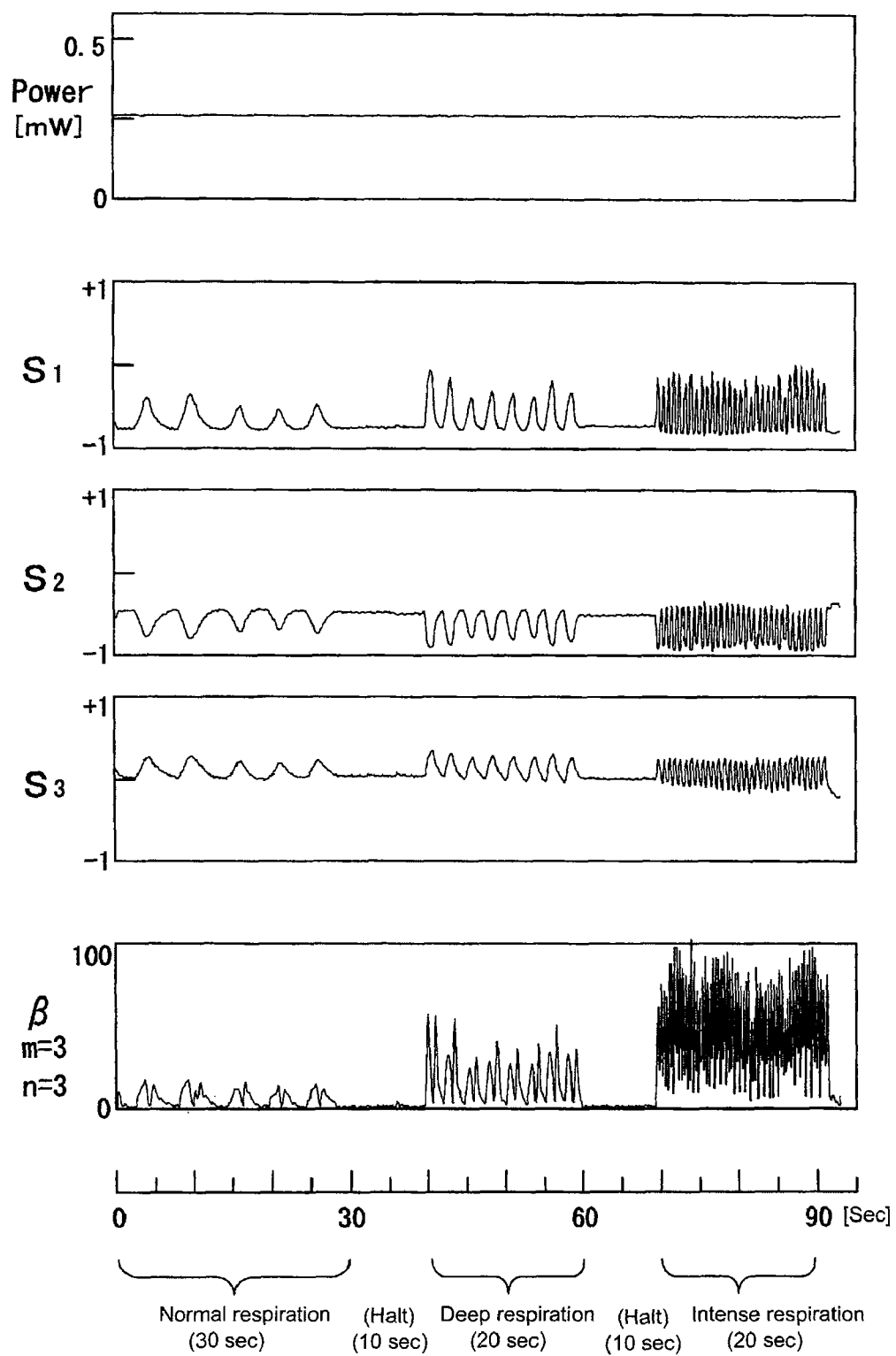
FIG. 20 demonstrates wave forms of an embodiment that show a relationship between respiration conditions of a human wearing a garment styled optical fiber type flat shaped body sensor and a polarized wave fluctuation quantity and a stokes parameter.

FIG. 20 illustrates the results for the above test including the measurement results of the time wave forms of the strength of light, the stokes parameters $S_1$, $S_2$, $S_3$, and the polarized wave fluctuation quantity at the time the test subject was in the lying position and wearing the garment styled optical fiber type flat shaped body sensor equipped with the 4-conductor optical fiber. Changes caused by respiration were distinctly detected by the waveforms of the stokes parameters S1, S2, S3 and by the polarized wave fluctuation quantity. Also, periodic changes were observed during periods of respiration. Furthermore, when normal respiration, deep respiration and intense respiration were compared, variations between the different respiration velocities were also observed.

With respect to the garment styled optical fiber type flat shaped body sensor, the magnitude of polarized wave fluctuations was found to be larger than those of a bed sheet (c.f., FIG. 18), and slightly smaller than those of a quilt cover when compared with test results collected in the case where sensor is used as a bed sheet, and a quilt cover, employing a 4-conductor optical fiber deployed in a wave shaped configuration. The same analysis as performed on the garment styled optical fiber type flat shaped body sensor was conducted on the aforementioned other 3 cases, and it was learned that polarized wave fluctuations caused by respiration were observed with each of the other cases.

In view of the results shown in FIG. 20, it is assumed that movements, such as respiration and the like, can be detected using polarized wave fluctuations occurring within a human body fitted optical fiber type flat shaped body sensor. For example, in the case of a human body fitted optical fiber type flat shaped body sensor fitted to the chest area, it is understood that, because the sensor can be fitted closely to the individual body shape when compared to the case of a garment styled sensor, polarized wave fluctuations equivalent to or better than those of FIG. 20 should result.

FEASIBILITY OF INDUSTRIAL USE

The present invention is mainly used for remote monitoring of patients, those cared for, and the like in nursing care facilities, hospitals and the like. Also, the present invention can be widely used for monitoring living activities of animals, plants, and the like other than humans. The present invention also makes it possible to intensively monitor patients and the like in hospitals or nursing care facilities covering a wide area by making use of a so-called communications network.

What is claimed is:

1. A method for monitoring living body activities involving monitoring human body movements and body activities of a human being sleeping on a bed, futon-bed, pad, or tatami-mat, wherein the method comprises the steps of:
   (a) disposing an optical fiber flat shaped body sensor comprising a flat shaped body and an optical fiber fitted to or integrated with the flat shaped body, so that living body activities and human body movements, respectively, change a form of the optical fiber flat shaped body sensor;
   (b) emitting a polarized light wave from a light source into the optical fiber and propagating the polarized wave of light along the optical fiber;
   (c) producing fluctuations in the polarized wave of light propagating along the optical fiber when living body activities or human body movements bring about changes in the form of the optical fiber flat shaped body sensor;
   (d) detecting fluctuations in the polarized wave of light using a polarized wave fluctuation measuring apparatus;
   (e) detecting periodic vibrations specific to respiration or heart pulsation by using a sum of a power spectrum of the fluctuations detected
      i. by the polarized wave fluctuation measuring apparatus; and
      ii. by time waveforms of three Stokes parameters, corresponding to polarized wave conditions of light, transformed using a Fourier Transform;
   (f) discriminating living body activities from human body movements using the detected fluctuations in the polarized wave of light, wherein by using the polarized wave fluctuation measuring apparatus living body activities or human body movements are detected at high speed and with high sensitivity based on a polarized wave fluctuation quantity, wherein the polarized wave fluctuation quantity is computed as a difference between a present value of a first polarized wave condition parameter, expressed by three Stokes parameters, and a second polarized wave condition parameter, found ¼ to ½ of a first period corresponding to periodic vibrations specific to respiration or heart pulsation prior to a time of the present value; and
   (g) processing the first polarized wave condition parameter and the second polarized wave condition parameter by sampling to obtain a moving average, and setting a width of the moving average to be ¼ to ½ of periodic vibrations specific to respiration or heart pulsation thereby removing random noise in signals employed for discriminating living body activities from human body movements.

2. The method for monitoring living body activities according to claim 1, wherein the flat shaped body is selected from the group consisting of a sheet, a bed sheet, a blanket, a mat, a pad, a tatami-mat, a floor cover and a carpet.

3. The method for monitoring living body activities according to claim 1, wherein when the human being intentionally kicks or knocks any given side of the flat shaped body, then signals are transmitted by the polarized wave fluctuation measuring apparatus.

4. The method for monitoring living body activities according to claim 1, wherein a plurality of additional optical fiber flat shaped body sensors, or a plurality of additional optical fibers disposed in blocks in the optical fiber flat shaped body sensor, are monitored in sequence by one polarized wave fluctuation measuring apparatus, wherein monitoring in sequence is provided by a light source apparatus and the polarized wave fluctuation measuring apparatus connected together so as to switch and connect to the plurality of additional optical fiber flat shaped body sensors or to the plurality of additional optical fibers disposed in blocks.

5. The method for measuring living body activities according to claim 1, wherein a plurality of additional optical fibers of the optical fiber flat shaped body sensor are monitored in sequence by one polarized wave fluctuation measuring apparatus, wherein light is emitted to the plurality of additional optical fibers of the optical fiber flat shaped body sensor from a wavelength variable light source by switching optical fibers in sequence using a wavelength separation filter.

6. The method for monitoring living body activities according to claim 1, wherein the optical fiber includes a plurality of blocks, and a specific block of the optical fiber is discriminated for monitoring using a delay time of light dispersed in the optical fiber by transmitting an optical pulse from one end of the optical fiber of the optical fiber flat shaped body sensor.

7. The method for monitoring living body activities according to claim 1, wherein movements of the human being are monitored from a distance, wherein the optical fiber flat shaped body sensor comprises a communication optical fiber and the optical fiber that is fitted to or integrated with the flat shaped body is connected to the communication optical fiber.

8. The method for monitoring living body activities according to claim 1, further comprising determining whether the fluctuations are aperiodic or periodic to discriminate between human body movements and living body activities, wherein the human body movements are selected from the group consisting of tossing and turning, and getting into bed and getting out of bed, and wherein the living body activities include respiration at rest or heart pulsation during periods of no respiration.

9. The method for monitoring living body activities according to claim 8, wherein polarized wave fluctuations of the human body movements are aperiodic and have a wide fluctuation range whereas the polarized wave fluctuations of the living body activities are periodic and have a narrow fluctuation range.

10. The method for monitoring living body activities according to claim 1, wherein the optical fiber includes a plurality of blocks, and specific blocks of the optical fiber are discriminated for monitoring by a plurality of filters reflecting specific wavelengths of light, wherein the plurality of filters are incorporated within the optical fiber of the optical fiber flat shaped body sensor so that wavelengths of the light source are filtered.

11. The method for monitoring living body activities according claim 10, wherein the specific wavelengths are reflected by optical fiber diffraction.

12. The method for measuring living body activities according to claim 1, wherein a plurality of blocks of the optical fiber in the optical fiber flat shaped body sensor are monitored in sequence by one polarized wave fluctuation measuring apparatus, wherein light is emitted to the plurality of blocks of the optical fiber in the optical fiber flat shaped body sensor from a wavelength variable light source by switching optical blocks in sequence using a wavelength separation filter.

* * * * *